(12) United States Patent
Samlowski et al.

(10) Patent No.: US 7,407,777 B2
(45) Date of Patent: Aug. 5, 2008

(54) IL-2 TRANSMEMBRANE CONSTRUCT

(75) Inventors: Wolfram Samlowski, Salt Lake City, UT (US); Nathan Bradley Adams, Colchester, VT (US); John McGregor, Salt Lake City, UT (US)

(73) Assignee: University of Utah Research Foundation, Salk Lake City, UT (US)

( * ) Notice: Subject to any disclaimer, the term of this patent is extended or adjusted under 35 U.S.C. 154(b) by 0 days.

(21) Appl. No.: 10/548,153

(22) PCT Filed: Mar. 8, 2004

(86) PCT No.: PCT/US2004/007012
§ 371 (c)(1), (2), (4) Date: Sep. 6, 2005

(87) PCT Pub. No.: WO2004/080404
PCT Pub. Date: Sep. 23, 2004

(65) Prior Publication Data
US 2006/0177908 A1     Aug. 10, 2006

Related U.S. Application Data

(60) Provisional application No. 60/452,989, filed on Mar. 7, 2003.

(51) Int. Cl.
C12N 5/10     (2006.01)
C12N 15/62    (2006.01)
C12N 15/63    (2006.01)

(52) U.S. Cl. .................. 435/69.7; 435/320.1; 435/325; 435/252.3; 536/23.4

(58) Field of Classification Search .................. None
See application file for complete search history.

(56) References Cited

U.S. PATENT DOCUMENTS 5,641,665 A     6/1997 Hobart

OTHER PUBLICATIONS

Vanderspek et al. "Structure/Function Analysis of the Transmembrane Domain of $DAB_{389}$- Interluekin-2, an Interluekin-2 Receptor-targeted Fusion Toxin." The Journal of Biological Chemistry, Jun. 1993, vol. 268, No. 16, pp. 12077-12082, especially pp. 12077-12078.

Belani R, Weiner GJ. Expression of both B7-1 and CD28 contributes to the IL-2 responsiveness of CTLL-2 cells. Immunology. Feb. 1996;87(2):271-4.

Eckenberg R, Rose T, Moreau JL, Weil R, Gesbert F, Dubois S, Tello D, Bossus M, Gras H, Tartar A, Bertoglio J, Chouaïb S, Goldberg M, Jacques Y, Alzari PM, Thèze J. The first alpha helix of interleukin (IL)-2 folds as a homotetramer, acts as an agonist of the IL-2 receptor beta chain, and induces lymphokine-activated killer cells. J Exp Med. Feb. 7, 2000;191(3):529-40.

El-Shami et al, Induction of antitumor immunity with modified autologous cells expressing membrane-bound murine cytokines. Inteferon and Cytokine Res.. 19:1391-1401 (1999).

Emtage et al., A Double Recombinant Adenovirus Expressing the Costimulatory Molecule B7-1 (Murine) and Human IL-2 Induces Complete Tumor Regression in a Murine Breast Adenocarcinoma Model, J. Immuno., 160: 2531-2538 (1998).

Fisher RI, Rosenberg SA, Sznol M, et al. High-dose aldesleukin in renal cell carcinoma: long-term survival update. Cancer J. Sci. Am., 3 (1997) S70-S72.

Grimm & Wilson, The human lymphokine-activated killer system. . . . blood lymphocytes, Cell Immunol., 94: 568-578 (1985).

Herblot S, Chastagner P, Samady L, Moreau JL, Demaison C, Froussard P, Liu X, Bonnet J, Thèze J. IL-2-dependent expression of genes involved in cytoskeleton organization, oncogene regulation, and transcriptional control. J Immunol. Mar. 15, 1999;162(6):3280-8.

Horton HM, Dorigo O, Hernandez P, Anderson D, Berek JS, Parker SE. IL-2 plasmid therapy of murine ovarian carcinoma inhibits the growth of tumor ascites and alters its cytokine profile. J Immunol. Dec. 15, 1999;163(12):6378-85.

Kurzrock, Cytokine: Interleukins and Their Receptors. Massachusetts: Kluwer Academic Publishers, 83-97. (1995).

Legha SS. 1997 Durable complete responses in metastatic melanoma treated with Interleukin-2 in combination with Interferon Alfa and Chemotherapy. Sem Oncol 24 ((2)) (S4-39-S4-43).

Li S, Huang L. Nonviral gene therapy: promises and challenges. Gene Ther. Jan. 2000;7(1):31-4.

Luo et al., Comparison of the Effects of Immunosuppressive Factors from Newly Established Colon Carcinoma Cell Cultures on Human Lymphocyte Proliferation and Cytokine Secretion, Tumor Biol., 21:11-20. (1999).

Marr RA, Addison CL, Snider D, Muller WJ, Gauldie J, Graham FL. Tumour immunotherapy using an adenoviral vector expressing a membrane-bound mutant of murine TNF alpha. Gene Ther. Nov. 1997;4(11):1181-8.

(Continued)

Primary Examiner—Prema Mertz
(74) Attorney, Agent, or Firm—The McCallum Law Firm, P.C.; Jennifer M. McCallum, Esq.

(57) ABSTRACT

Compounds, genetic constructs, and cancer treatment methods are provided. Expression vectors were designed to express fusion genes including hIL-2 with a Fcε-γ transmembrane anchor derived from a subunit of the FC epsilon receptor. mRNA and the IL-2tm fusion protein was expressed in transfected RD995 tumor cells. Expression of the IL-2tm protein on the tumor cell surface membrane was confirmed by microscopy. RD995 cells transfected with IL-2tm or pCMV2b (empty expression vector) were implanted subcutaneously into C3H/HEN mice. Tumors of mice implanted with $10^6$ or $10^5$ RD995 cells transfected with IL-2tm grew slower than controls. It is believed that selective expression of cytokines such as IL-2 on the surface of tumors is likely to stimulate tumor-infiltrating lymphocytes that are primed and already recognize tumor antigens, enhancing tumor recognition and killing, potentially avoiding toxicity associated with known cytokine therapies.

18 Claims, 22 Drawing Sheets

OTHER PUBLICATIONS

Mertelsmann R, Welte K. Human Interleukin 2: molecular biology, physiology and clinical possibilities. Immunobiol. 1986;172:400-19.

Rochlitz et al., Gene Therapy Study of Cytokine-Transfected Xenogeneic Cells (†Vera-interleukin-2) in Patients with Metastatic Solid Tumors, Cancer Gene Therapy, 6:271-281, (1999).

Rosenberg, SA, BS Packard, PM Aebersold, D Solomon, SL Topalian, ST Toy, P Simon, MT Lotze, JC Yang, CA Seipp, and et al. Use of tumor-infiltrating lymphocytes and interleukin-2 in the immunotherapy of patients with metastatic melanoma. A preliminary report (1988) New England Journal of Medicine vol. 319:1676-1680.

Schneeberger, et al, The tumorigenicity of IL-2 gene-transfected murine M-3D melanoma cells is determined by the magnitude and quality of the host defense reaction: NK cells play a major role., J. Immunol. 162:6650-6657. (1999).

Siegel & Puri, Interleukin-2 toxicity, .J Clin. Oncol, 9: 694-704 (1991).

Topalian et al., Tumor-specific cytolysis by lymphocytes infiltrating human melanomas, J. Immunol, 142:3714. (1989).

Vanderspek, J. et al, "DAB-389 interleukin-2 receptor binding domain mutations: Cytotoxic probes for studies of ligand-receptor interactions" Journal Biological Chemistry vol. 271 No. 21, pp. 12145-12149, (1996).

Vile RG, Russell SJ, Lemoine NR. Gene Ther. Cancer gene therapy: hard lessons and new courses. Jan. 2000;7(1):2-8.

Yao L, Sgadari C, Furuke K, Bloom ET, Teruya-Feldstein J, Tosato G. Contribution of natural killer cells to inhibition of angiogenesis by interleukin-12. Blood. Mar. 1, 1999;93(5):1612-21.

```
CACAAACAGTGCACCTACTTCAAGTTCTACAAAGAAAACACAGCTACAACTGGAG
CATTTACTGCTGGATTTACAGATGATTTTGAATGGAATTAATAATTACAAGAATCC
CAAACTCACCAGGATGCTCACATTTAAGTTTTACATGCCCAAGAAGGCCACAGAAC
TGAAACATCTTCAGTGTCTAGAAGAAGAACTCAAACCTCTGGAGGAAGTGCTAAAT
TTAGCTCAAAGCAAAAACTTTCACTTAAGACCCAGGGACTTAATCAGCAATATCAA
CGTAATAGTTCTGGAACTAAAGGGATCTGAAACAACATTCATGTGTGAATATGCTG
ATGAGACAGCAACCATTGTAGAATTTCTGAACAGATGGATTACCTTTTGTCAAAGC
ATCATCTCAACACTGACTTGATAATTAAGTGCTTCCCACTTAAAACATATCAGGGA
TCTCGACTCTAGAGGATCAAC
```

Figure 3

```
TCCGCACCTACTTCAAGTTCTACAAAGAAAACACAGCTACAACTGGAGCATTTA
CTGCTGGATTTACAGATGATTTTGAATGGAATTAATAATTACAAGAATCCCAAACT
CACCAGGATGCTCACATTTAAGTTTTACATGCCCAAGAAGGCCACAGAACTGAAAC
ATCTTCAGTGTCTAGAAGAAGAACTCAAACCTCTGGAGGAAGTGCTAAATTTAGCT
CAAAGCAAAAACTTTCACTTAAGACCCAGGGACTTAATCAGCAATATCAACGTAAT
AGTTCTGGAACTAAAGGGATCTGAAACAACATTCATGTGTGAATATGCTGATGAGA
CAGCAACCATTGTAGAATTTCTGAACAGATGGATTACCTTTTGTCAAAGCATCTCA
ACACTGACTGAATTCGGCACGAGGGCCGATCTCCAGCCAGATGATTCACCAGCA
GTGGTCTTGCTCTTACTCCTTTTGGTTGAACAAGCAGCGGCCCTGGGAGAGCCTCA
```

Figure 5

```
TGGAGCTCCCCGCGGTGGCGGCCGCCCCATGGATTACAAGGATGACGACGATAAGAG
CCCGGGCGGATCCGCACCTACTTCAAGTTCTACAAAGAAAACACAGCTACAACTGGAGC
ATTTACTGCTGGATTTACAGATGATTTTGAATGGAATTAATAATTACAAGAATCCCAAAC
TCACCAGGATGCTCACATTTAAGTTTTACATGCCCAAGAAGGCCACAGAACTGAAACAT
CTTCAGTGTCTAGAAGAAGAACTCAAACCTCTGGAGGAAGTGCTAAATTTAGCTCAAAG
CAAAAACTTTCACTTAAGACCCAGGGACTTAATCAGCAATATCAACGTAATAGTTCTGG
AACTAAAGGGATCTGAAACAACATTCATGTGTGAATATGCTGATGAGACAGCAACCATT
GTAGAATTTCTGAACAGATGGATTACCTTTTGTCAAAGCATCTCAACACTGACTGAATTC
GGCACGAGGGCCGATCTCCAGCCCAAGATGATTCCAGCAGTGGTCTTGCTCTTACTCC
TTTTGGTTGAACAAGCAGCGGCCCTGGGAGAGCCTCAGCTCTGCTATATCCTGGATGCC
ATCCTGTTTCTGTATGGAATTGTCCTCACCCTCCTCTACTGTCGACTGAAGATCCAAGTG
CGAAAGGCAGCTATAACCAGCTATGAGAAATCAGATGGTGTTTACACGGGCCTGAGCAC
CAGGAACCAGGAGACTTACAAGACTCTGAAGCATGAGAAACCACCACAGTAGCTTTAG
AATAGATGCGGNCATATTCTTCTTTGGCTTCTGGGTCTTNCAGCCCTCATGGGTGGCATC
ACATATGCCTGCATGCCATTAACACCAGCTGGGCCTACCCCTATNATGGATCCTGNGTCC
TAAATTATATACACCCAGNGGGTCTGGAGCTCCCCGCGGTGGCGGCCGCCCCATGGATT
ACAAGGATGACGACGATAAGAGCCCGGGCGGATCCGCACCTACTT
CAAGTTCTACAAAGAAAACAGCTACAACTGGAGCATTTACTGCTGGATTTACAGATG
ATTTTGAATGGAATTAATAAT
TACAAGAATCCCAAACTCACCAGGATGCTCACATTTAAGTTTTACATGCCCAAGAAGGC
CACAGAACTGAAACATCTTCA
GTGTCTAGAAGAAGAACTCAAACCTCTGGAGGAAGTGCTAAATTTAGCTCAAAGCAAAA
ACTTTCACTTAAGACCCAGGG
ACTTAATCAGCAATATCAACGTAATAGTTCTGGAACTAAAGGGATCTGAAACAACATTC
ATGTGTGAATATGCTGATGAG
ACAGCAACCATTGTAGAATTTCTGAACAGATGGATTACCTTTTGTCAAAGCATCTCAACA
CTGACTGAATTCGGCACGAG
GGCCGATCTCCAGCCCAAGATGATTCCAGCAGTGGTCTTGCTCTTACTCCTTTTGGTTGA
ACAAGCAGCGGCCCTGGGAG
AGCCTCAGCTCTGCTATATCCTGGATGCCATCCTGTTTCTGTATGGAATTGTCCTCACCCT
CCTCTACTGTCGACTGAAG
ATCCAAGTGCGAAAGGCAGCTATAACCAGCTATGAGAAATCAGATGGTGTTTACACGGG
CCTGAGCACCAGGAACCAGGA
GACTTACAAGACTCTGAAGCATGAGAAACCACCACAGTAGCTTTAGAATAGATGCGGNC
ATATTCTTCTTTGGCTTCTGG
GTCTTNCAGCCCTCATGGGTGGCATCACATATGCCTGCATGCCATTAACACCAGCTGGGC
CTACCCCTATNATGGATCCT
GNGTCCTAAATTATATACACCCAGNGGGTC
```

Figure 6

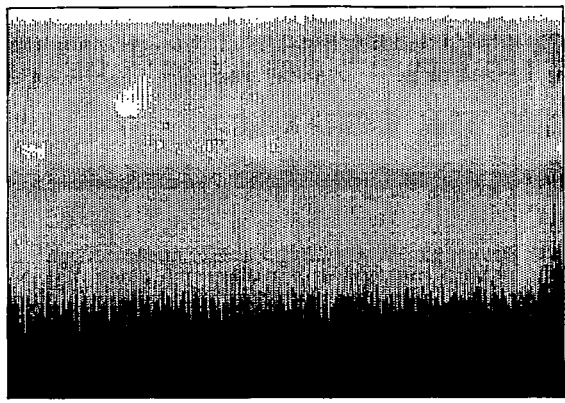
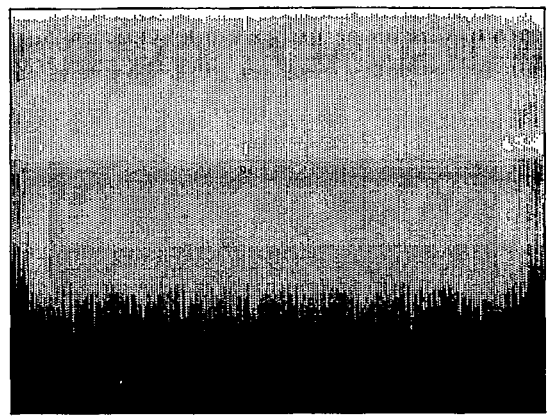
A　　　　　　　　　　　　B
Figure 9

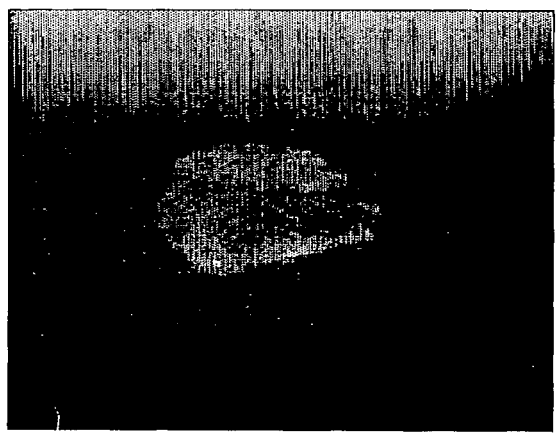 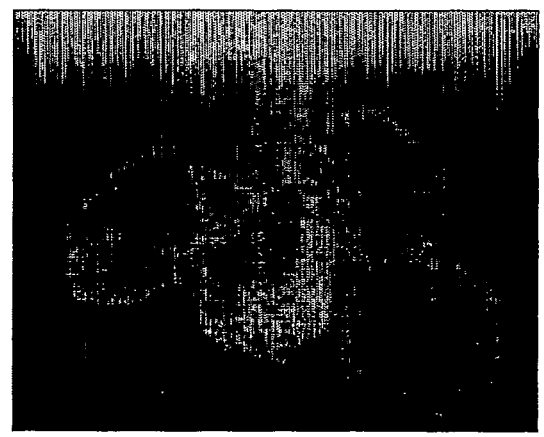
A          B
Figure 10

| 1 | GCTGGAGCTC | CCCGCGGTGG | CGGCCGCCCC | TGGNATTACA | AGGATGACGA |
|---|---|---|---|---|---|
| 51 | CGATAAGAGC | CCGGGCGGAT | CCGCACCTAC | TTCAAGTTCT | ACAAAGAAAA |
| 101 | CACAGCTACA | ACTGGAGCAT | TTACTGCTGG | ATTTACAGAT | GATTTTGAAT |
| 151 | GGAATTAATA | ATTACAAGAA | TCCCAAACTC | ACCAGGATGC | TCACATTTAA |
| 201 | GTTTTACATG | CCCAAGAAGG | CCACAGAACT | GAAACATCTT | CAGTGTCTAG |
| 251 | AAGAAGAACT | CAAACCTCTG | GAGGAAGTGC | TAAATTTAGC | TCAAAGCAAA |
| 301 | AACTTTCACT | TAAGACCCAG | GGACTTAATC | AGCAATATCA | ACGTAATAGT |
| 351 | TCTGGAACTA | AAGGGATCTG | AAACAACATT | CATGTGTGAA | TATGCTGATG |
| 401 | AGACAGCAAC | CATTGTAGAA | TTTCTGAACA | GATGGATTAC | CTTTTGTCAA |
| 451 | AGCATCTCAA | CACTGACTGA | ATTCGGCACG | AGGGCCGATC | TCCAGCCCAA |
| 501 | GATGATTCCA | GCAGTGGTCT | TGCTCTTACT | CCTTTTGGTT | GAACAAGCAG |
| 551 | CGGCCCTGGG | AGAGCCTCAG | CTCTGCTATA | TCCTGGATGC | CATCCTGTTT |
| 601 | CTGTATGGAA | TTGTCCTCAC | CCTCCTCTAC | TGTCGACTGA | AGATCCAAGT |
| 651 | GCGAAAGGCA | GCTATAACCA | GCTATGAGAA | ATCAGATGGT | GTTTACACGG |
| 701 | GCCTGAGCAC | CAGGAACCAG | GAGACTTACA | AGACTCTGAA | GCATGAGAAA |
| 751 | CCACCACAGT | AGCTTTAGAA | TAGATGCNGG | CATATTCTTC | TTTGGCTTCT |
| 801 | GGGTCTTTCA | GCCCTCATGG | GTNGGCATCA | CATATGCCTG | CATGCCATTN |
| 851 | ACACCAGCTG | GNCCTACCCC | TATAANGATC | CTGNGTCCTA | AATTAATATA |
| 901 | CACCAGGGGG | TTCCTNCTNC | CTGTTAAANA | CTAC | |

Figure 14

```
  1 TGAATTCGGC ACGAGGGCCG ATCTCCAGCC CAAGATGATT CCAGCAGTGG
 51 TCTTGCTCTT ACTCCTTTTG GTTGAACAAG CAGCGGCCCT GGGAGAGCCT
101 CAGCTCTGCT ATATCCTGGA TGCCATCCTG TTTCTGTATG GAATTGTCCT
151 CACCCTCCTC TACTGTCGAC TGAAGATCCA AGTGCGAAAG GCAGCTATAA
201 CCAGCTATGA GAAATCAGAT GGTGTTTACA CGGGCCTGAG CACCAGGAAC
251 CAGGAGACTT ACAAGACTCT GAAGCATGAG AAACCACCAC AGTAGCTTTA
301 GAATAGATG
```

Figure 15

| 1 | AGAPRGGGRP | WXYKDDDDKS | PGGSAPTSSS | TKKTQLQLEH | LLLDLQMILN |
|---|---|---|---|---|---|
| 151 | GINNYKNPKL | TRMLTFKFYM | PKKATELKHL | QCLEEELKPL | EEVLNLAQSK |
| 301 | NFHLRPRDLI | SNINVIVLEL | KGSETTFMCE | YADETATIVE | FLNRWITFCQ |
| 451 | SISTLTEFGT | RADLQPKMIP | AVVLLLLLLV | EQAAALGEPQ | LCYILDAILF |
| 601 | LYGIVLTLLY | CRLKIQVRKA | AITSYEKSDG | VYTGLSTRNQ | ETYKTLKHEK |
| 751 | PPQ-L-NRCX | HILLWLLGLS | ALMGXHHICL | HAIXTSWXYP | YkDPXS-INI |
| 901 | HQGVPXXC-X | LX | | | |

Figure 16

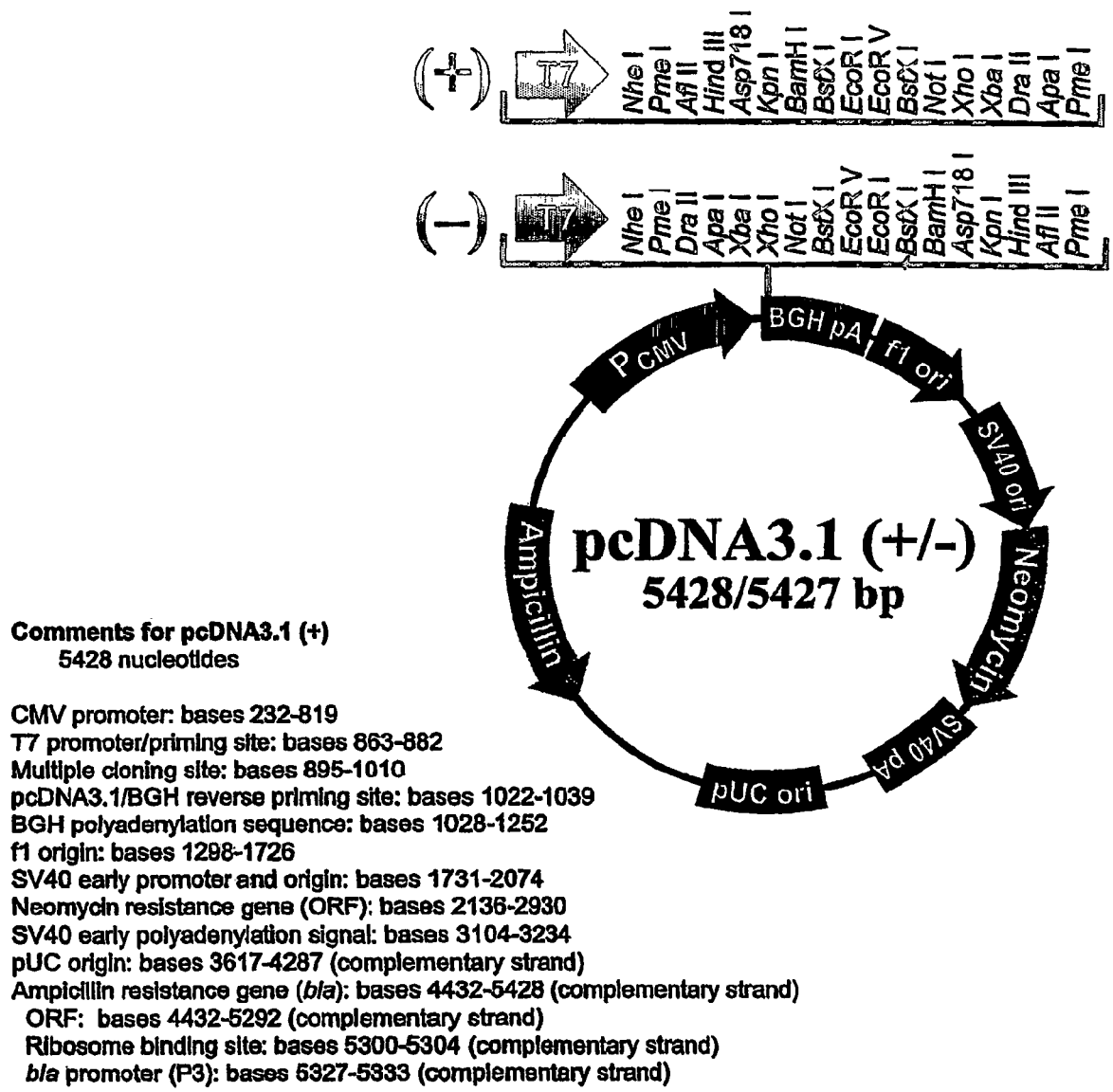

Comments for pcDNA3.1 (+)
5428 nucleotides

CMV promoter: bases 232-819
T7 promoter/priming site: bases 863-882
Multiple cloning site: bases 895-1010
pcDNA3.1/BGH reverse priming site: bases 1022-1039
BGH polyadenylation sequence: bases 1028-1252
f1 origin: bases 1298-1726
SV40 early promoter and origin: bases 1731-2074
Neomycin resistance gene (ORF): bases 2136-2930
SV40 early polyadenylation signal: bases 3104-3234
pUC origin: bases 3617-4287 (complementary strand)
Ampicillin resistance gene (*bla*): bases 4432-5428 (complementary strand)
 ORF: bases 4432-5292 (complementary strand)
 Ribosome binding site: bases 5300-5304 (complementary strand)
 *bla* promoter (P3): bases 5327-5333 (complementary strand)

Figure 18

Notes:

Modifications from IL-2TM include the following:

1. FC-gamma-epsilon has been truncated to include only one transmembrane domain

2. FLAG has been removed

3. Extra nucleotides in the multiple cloning site have been removed

4. IL-2+FC-gamma-epsilon has been inserted into a high expression vector that includes an enhancer for the CMV promoter

|   |   |   |   |   |   |
|---|---|---|---|---|---|
| 2   | QLASV-T-AW | YRARIPATMA | PTSSSTKKTQ | LQLEHLLLDL | QMILNGINNY |
| 152 | KNPKLTRMLT | FKFYMPKKAT | ELKHLQCLEE | ELKPLEEVLN | LAQSKNFHLR |
| 302 | PRDLISNINV | IVLELKGSET | TFMCEYADET | ATIVEFLNRW | ITFCQSISTL |
| 452 | TEFGTRADLQ | PKMIPAVVLL | LLLLVEQAAA | LGEPQLCYIL | DAILFLYGIV |
| 602 | LTLLYCRDDP | LESRGPV-TR | -SASTVPSSC | QPSVVCPSPV | PSLTLEGXTP |
| 752 | TVLS--NEEI | ASHCLSXCHS | ILGGGVGAGQ | QXGRIGKTIA | GMX |

Figure 20

|     |            |            |            |            |            |
|-----|------------|------------|------------|------------|------------|
| 1   | AGAPRGGGRP | WKYKDDDDKS | PGGSAPTSSS | TKKTQLQLEH | LLLDLQMILN |
| 151 | GINNYKNPKL | TRMLTFKFYM | PKKATELKHL | QCLEEELKPL | EEVLNLAQSK |
| 301 | NFHLRPRDLI | SNINVIVLEL | KGSETTFMCE | YADETATIVE | FLNRWITFCQ |
| 451 | SISTLTEFGT | RADLQPKMIP | AVVLLLLLV  | EQAAALGEPQ | LCYILDAILF |
| 601 | LYGIVLTLLY | CRLKIQVRKA | AITSYEKSDG | VYTGLSTRNQ | ETYKTLKHEK |
| 751 | PPQ-L-NRCX | HILLWLLGLS | ALMGXHHICL | HAIXTSWXYP | YkDPXS-INI |
| 901 | HQGVPXXC-X | LX         |            |            |            |

Figure 21

| 1   | CCAGCTGGCT | AGCGTTTAAA | CTTAAGCTTG | GTACCGAGCT | CGGATCCCGG |
|-----|------------|------------|------------|------------|------------|
| 51  | CCACCATGGC | ACCTACTTCA | AGTTCTACAA | AGAAAACACA | GCTACAACTG |
| 101 | GAGCATTTAC | TGCTGGATTT | ACAGATGATT | TTGAATGGAA | TTAATAATTA |
| 151 | CAAGAATCCC | AAACTCACCA | GGATGCTCAC | ATTTAAGTTT | TACATGCCCA |
| 201 | AGAAGGCCAC | AGAACTGAAA | CATCTTCAGT | GTCTAGAAGA | AGAACTCAAA |
| 251 | CCTCTGGAGG | AAGTGCTAAA | TTTAGCTCAA | AGCAAAAACT | TTCACTTAAG |
| 301 | ACCCAGGGAC | TTAATCAGCA | ATATCAACGT | AATAGTTCTG | GAACTAAAGG |
| 351 | GATCTGAAAC | AACATTCATG | TGTGAATATG | CTGATGAGAC | AGCAACCATT |
| 401 | GTAGAATTTC | TGAACAGATG | GATTACCTTT | TGTCAAAGCA | TCTCAACACT |
| 451 | GACTGAATTC | GGCACGAGGG | CCGATCTCCA | GCCCAAGATG | ATTCCAGCAG |
| 501 | TGGTCTTGCT | CTTACTCCTT | TTGGTTGAAC | AAGCAGCGGC | CCTGGGAGAG |
| 551 | CCTCAGCTCT | GCTATATCCT | GGATGCCATC | CTGTTTCTGT | ATGGAATTGT |
| 601 | CCTCACCCTC | CTCTACTGTC | GAGATGATCC | GCTCGAGTCT | AGAGGGCCCG |
| 651 | TTTAAACCCG | CTGATCAGCC | TCGACTGTGC | CTTCTAGTTG | CCAGCCATCT |
| 701 | GTTGTTTGCC | CCTCCCCGT  | GCCTTCCTTG | ACCCTGGAAG | GTGNCACTCC |
| 751 | CACTGTCCTT | TCCTAATAAA | ATGAGGAAAT | TGCATCGCAT | TGTCTGAGTA |
| 801 | NGTGTCATTC | TATTCTGGGG | GGTGGGGTGG | GGGCAGGACA | GCAANGGGGG |
| 851 | AGGATTGGGA | AGACAATAGC | AGGCATGNCT |            |            |

Figure 22

SEQUENCE LISTING

```
<160> NUMBER OF SEQ ID NOS: 15

<210> SEQ ID NO 1
<211> LENGTH: 468
<212> TYPE: DNA
<213> ORGANISM: Homo sapiens

<400> SEQUENCE: 1
cacaaacagt gcacctactt caagttctac aaagaaaaca cagctacaac tggagcattt      60
actgctggat ttacagatga ttttgaatgg aattaataat tacaagaatc ccaaactcac     120
caggatgctc acatttaagt tttacatgcc caagaaggcc acagaactga acatcttca     180 gtgtctagaa gaagaactca aacctctgga ggaagtgcta aatttagctc aaagcaaaaa     240
ctttcactta agacccaggg acttaatcag caatatcaac gtaatagttc tggaactaaa     300
gggatctgaa acaacattca tgtgtgaata tgctgatgag acagcaacca ttgtagaatt     360
tctgaacaga tggattacct tttgtcaaag catcatctca acactgactt gataattaag     420
tgcttcccac ttaaaacata tcagggatct cgactctaga ggatcaac                  468

<210> SEQ ID NO 2
<211> LENGTH: 500
<212> TYPE: DNA
<213> ORGANISM: Artificial
<220> FEATURE:
<223> OTHER INFORMATION: Sequence of the hIL-2 + Fc EPSILON-GAMMA
      fusion gene construct.

<400> SEQUENCE: 2
tccgcaccta cttcaagttc tacaaagaaa acacagctac aactggagca tttactgctg      60
gatttacaga tgattttgaa tggaattaat aattacaaga atcccaaact caccaggatg     120
ctcacattta gtttttacat gcccaagaag gccacagaac tgaaacatct tcagtgtcta     180
gaagaagaac tcaaacctct ggaggaagtg ctaaatttag ctcaaagcaa aaactttcac     240
ttaagaccca gggacttaat cagcaatatc aacgtaatag ttctggaact aaagggatct     300
```

```
gaaacaacat tcatgtgtga atatgctgat gagacagcaa ccattgtaga atttctgaac      360
agatggatta ccttttgtca aagcatctca acactgactg aattcggcac gagggccgat      420
ctccagccag atgattcacc agcagtggtc ttgctcttac tccttttggt tgaacaagca      480
gcggccctgg gagagcctca                                                  500

<210> SEQ ID NO 3
<211> LENGTH: 1820
<212> TYPE: DNA
<213> ORGANISM: Artificial Sequence
<220> FEATURE:
<223> OTHER INFORMATION: Sequence of the hIL-2tm construct ligated in
      the proper reading frame into a pCMV2b mammalian expression
      vector.
<220> FEATURE:
<221> NAME/KEY: misc_feature
<222> LOCATION: (778)..(778)
<223> OTHER INFORMATION: n is a, c, g, or t
<220> FEATURE:
<221> NAME/KEY: misc_feature
<222> LOCATION: (806)..(806)
<223> OTHER INFORMATION: n is a, c, g, or t
<220> FEATURE:
<221> NAME/KEY: misc_feature
<222> LOCATION: (871)..(871)
<223> OTHER INFORMATION: n is a, c, g, or t
<220> FEATURE:
<221> NAME/KEY: misc_feature
<222> LOCATION: (882)..(882)
<223> OTHER INFORMATION: n is a, c, g, or t
<220> FEATURE:
<221> NAME/KEY: misc_feature
<222> LOCATION: (905)..(905)
<223> OTHER INFORMATION: n is a, c, g, or t
<220> FEATURE:
<221> NAME/KEY: misc_feature
<222> LOCATION: (1688)..(1688)
<223> OTHER INFORMATION: n is a, c, g, or t
<220> FEATURE:
<221> NAME/KEY: misc_feature
<222> LOCATION: (1716)..(1716)
<223> OTHER INFORMATION: n is a, c, g, or t
<220> FEATURE:
<221> NAME/KEY: misc_feature
<222> LOCATION: (1781)..(1781)
<223> OTHER INFORMATION: n is a, c, g, or t
<220> FEATURE:
<221> NAME/KEY: misc_feature
<222> LOCATION: (1792)..(1792)
<223> OTHER INFORMATION: n is a, c, g, or t
<220> FEATURE:
<221> NAME/KEY: misc_feature
<222> LOCATION: (1815)..(1815)
<223> OTHER INFORMATION: n is a, c, g, or t

<400> SEQUENCE: 3
tggagctccc cgcggtggcg gccgcccat ggattacaag gatgacgacg ataagagccc       60
gggcggatcc gcacctactt caagttctac aaagaaaaca cagctacaac tggagcattt     120
actgctggat ttacagatga ttttgaatgg aattaataat acaagaatcc caaactcac     180 caggatgctc acatttaagt tttacatgcc aagaaggcc acagaactga acatcttca      240 gtgtctagaa gaagaactca aacctctgga ggaagtgcta aatttagctc aaagcaaaaa    300 cttttcactta agacccaggg acttaatcag caatatcaac gtaatagttc tggaactaaa   360
gggatctgaa acaacattca tgtgtgaata tgctgatgag acagcaacca ttgtagaatt   420
tctgaacaga tggattacct tttgtcaaag catctcaaca ctgactgaat cggcacgag    480 ggccgatctc cagcccaaga tgattccagc agtggtcttg ctcttactcc ttttggttga    540
acaagcagcg gccctgggag agcctcagct ctgctatatc ctggatgcca tcctgttct    600
```

-continued

```
gtatggaatt gtcctcaccc tcctctactg tcgactgaag atccaagtgc gaaaggcagc    660
tataaccagc tatgagaaat cagatggtgt ttacacgggc ctgagcacca ggaaccagga    720
gacttacaag actctgaagc atgagaaacc accacagtag ctttagaata gatgcggnca    780
tattcttctt tggcttctgg gtcttncagc cctcatgggt ggcatcacat atgcctgcat    840
gccattaaca ccagctgggc ctaccccctat natggatcct gngtcctaaa ttatatacac    900
ccagngggtc tggagctccc cgcggtggcg gccgcccat ggattacaag gatgacgacg    960
ataagagccc gggcggatcc gcacctactt caagttctac aaagaaaaca cagctacaac   1020
tggagcattt actgctggat tttgaatga ttttgaatgg aattaataat tacaagaatc   1080
ccaaactcac caggatgctc acatttaagt tttacatgcc caagaaggcc acagaactga   1140
aacatcttca gtgtctagaa gaagaactca aacctctgga ggaagtgcta aatttagctc   1200
aaagcaaaaa ctttcactta agacccaggg acttaatcag caatatcaac gtaatagttc   1260
tggaactaaa gggatctgaa acaacattca tgtgtgaata tgctgatgag acagcaacca   1320
ttgtagaatt tctgaacaga tggattacct tttgtcaaag catctcaaca ctgactgaat   1380
tcggcacgag ggccgatctc cagcccaaga tgattccagc agtggtcttg ctcttactcc   1440
ttttggttga acaagcagcg gccctgggag agcctcagct ctgctatatc ctggatgcca   1500 tcctgttttct gtatggaatt gtcctcaccc tcctctactg tcgactgaag atccaagtgc   1560
gaaaggcagc tataaccagc tatgagaaat cagatggtgt ttacacgggc ctgagcacca   1620
ggaaccagga gacttacaag actctgaagc atgagaaacc accacagtag ctttagaata   1680
gatgcggnca tattcttctt tggcttctgg gtcttncagc cctcatgggt ggcatcacat   1740
atgcctgcat gccattaaca ccagctgggc ctaccccctat natggatcct gngtcctaaa   1800
ttatatacac ccagngggtc                                              1820
```

<210> SEQ ID NO 4
<211> LENGTH: 7
<212> TYPE: DNA
<213> ORGANISM: Homo sapiens
<400> SEQUENCE: 4 taattaa                                                                7

<210> SEQ ID NO 5
<211> LENGTH: 6
<212> TYPE: DNA
<213> ORGANISM: Artificial sequence
<220> FEATURE:
<223> OTHER INFORMATION: PCR primer for incorporation of BamHI
      restriction site.

<400> SEQUENCE: 5 ggatcc                                                                 6

<210> SEQ ID NO 6
<211> LENGTH: 6
<212> TYPE: DNA
<213> ORGANISM: Artificial sequence
<220> FEATURE:
<223> OTHER INFORMATION: PCR primer for addiing EcoRI
      restriction site.

<400> SEQUENCE: 6 gaattc                                                                 6

```
<210> SEQ ID NO 7
<211> LENGTH: 21
<212> TYPE: DNA
<213> ORGANISM: Artificial sequence
<220> FEATURE:
<223> OTHER INFORMATION: PCR primer used to confirm insertion of
      intact hIL-2.

<400> SEQUENCE: 7
tgctggattt acagatgatt t                                              21

<210> SEQ ID NO 8
<211> LENGTH: 19
<212> TYPE: DNA
<213> ORGANISM: Artificial sequence
<220> FEATURE:
<223> OTHER INFORMATION: PCR primer used to confirm insertion of
      intact hIL-2.

<400> SEQUENCE: 8
cacttcctcc agaggtttg                                                 19

<210> SEQ ID NO 9
<211> LENGTH: 33
<212> TYPE: DNA
<213> ORGANISM: Artificial
<220> FEATURE:
<223> OTHER INFORMATION: PCR primer used to remove stop codon of the
      hIL-2 gene and add a BamHI restriction site.

<400> SEQUENCE: 9
agaactagtg gatccgcacc tacttcaagt tct                                 33

<210> SEQ ID NO 10
<211> LENGTH: 34
<212> TYPE: DNA
<213> ORGANISM: Artificial sequence
<220> FEATURE:
<223> OTHER INFORMATION: PCR primer used to remove stop codon of the
      hIL-2 gene and add a EcoRI restriction site.

<400> SEQUENCE: 10
gtcagggaat tcagtcagtg ttgagatagc tttg                                34

<210> SEQ ID NO 11
<211> LENGTH: 312
<212> TYPE: PRT
<213> ORGANISM: Artificial sequence
<220> FEATURE:
<223> OTHER INFORMATION: IL-2tm fusion protein sequence.
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (254)..(254)
<223> OTHER INFORMATION: Xaa can be any naturally occurring amino acid
<220> FEATURE:
<221> NAME/KEY: misc_feature
<222> LOCATION: (256)..(256)
<223> OTHER INFORMATION: Xaa can be any naturally occurring amino acid
<220> FEATURE:
<221> NAME/KEY: misc_feature
<222> LOCATION: (260)..(260)
<223> OTHER INFORMATION: Xaa can be any naturally occurring amino acid
<220> FEATURE:
<221> NAME/KEY: misc_feature
<222> LOCATION: (275)..(275)
<223> OTHER INFORMATION: Xaa can be any naturally occurring amino acid
```

```
<220> FEATURE:
<221> NAME/KEY: misc_feature
<222> LOCATION: (284)..(284)
<223> OTHER INFORMATION: Xaa can be any naturally occurring amino acid
<220> FEATURE:
<221> NAME/KEY: misc_feature
<222> LOCATION: (288)..(288)
<223> OTHER INFORMATION: Xaa can be any naturally occurring amino acid
<220> FEATURE:
<221> NAME/KEY: misc_feature
<222> LOCATION: (295)..(295)
<223> OTHER INFORMATION: Xaa can be any naturally occurring amino acid
<220> FEATURE:
<221> NAME/KEY: misc_feature
<222> LOCATION: (297)..(297)
<223> OTHER INFORMATION: Xaa can be any naturally occurring amino acid
<220> FEATURE:
<221> NAME/KEY: misc_feature
<222> LOCATION: (306)..(307)
<223> OTHER INFORMATION: Xaa can be any naturally occurring amino acid
<220> FEATURE:
<221> NAME/KEY: misc_feature
<222> LOCATION: (309)..(310)
<223> OTHER INFORMATION: Xaa can be any naturally occurring amino acid
<220> FEATURE:
<221> NAME/KEY: misc_feature
<222> LOCATION: (312)..(312)
<223> OTHER INFORMATION: Xaa can be any naturally occurring amino acid

<400> SEQUENCE: 11

Ala Gly Ala Pro Arg Gly Gly Gly Arg Pro Trp Xaa Tyr Lys Asp Asp
1               5                   10                  15

Asp Asp Lys Ser Pro Gly Gly Ser Ala Pro Thr Ser Ser Ser Thr Lys
            20                  25                  30

Lys Thr Gln Leu Gln Leu Glu His Leu Leu Leu Asp Leu Gln Met Ile
        35                  40                  45

Leu Asn Gly Ile Asn Asn Tyr Lys Asn Pro Lys Leu Thr Arg Met Leu
    50                  55                  60

Thr Phe Lys Phe Tyr Met Pro Lys Lys Ala Thr Glu Leu Lys His Leu
65                  70                  75                  80

Gln Cys Leu Glu Glu Glu Leu Lys Pro Leu Glu Glu Val Leu Asn Leu
                85                  90                  95

Ala Gln Ser Lys Asn Phe His Leu Arg Pro Arg Asp Leu Ile Ser Asn
            100                 105                 110

Ile Asn Val Ile Val Leu Glu Leu Lys Gly Ser Glu Thr Thr Phe Met
        115                 120                 125

Cys Glu Tyr Ala Asp Glu Thr Ala Thr Ile Val Glu Phe Leu Asn Arg
    130                 135                 140

Trp Ile Thr Phe Cys Gln Ser Ile Ser Thr Leu Thr Glu Phe Gly Thr
145                 150                 155                 160

Arg Ala Asp Leu Gln Pro Lys Met Ile Pro Ala Val Val Leu Leu Leu
                165                 170                 175

Leu Leu Leu Val Glu Gln Ala Ala Ala Leu Gly Glu Pro Gln Leu Cys
            180                 185                 190

Tyr Ile Leu Asp Ala Ile Leu Phe Leu Tyr Gly Ile Val Leu Thr Leu
        195                 200                 205

Leu Tyr Cys Arg Leu Lys Ile Gln Val Arg Lys Ala Ala Ile Thr Ser
    210                 215                 220

Tyr Glu Lys Ser Asp Gly Val Tyr Thr Gly Leu Ser Thr Arg Asn Gln
225                 230                 235                 240

Glu Thr Tyr Lys Thr Leu Lys His Glu Lys Pro Pro Gln Xaa Leu Xaa
                245                 250                 255
```

-continued

```
Asn Arg Cys Xaa His Ile Leu Leu Trp Leu Leu Gly Leu Ser Ala Leu
                260                 265                 270

Met Gly Xaa His His Ile Cys Leu His Ala Ile Xaa Thr Ser Trp Xaa
            275                 280                 285

Tyr Pro Tyr Lys Asp Pro Xaa Ser Xaa Ile Asn Ile His Gln Gly Val
        290                 295                 300

Pro Xaa Xaa Cys Xaa Xaa Leu Xaa
305                 310

<210> SEQ ID NO 12
<211> LENGTH: 293
<212> TYPE: PRT
<213> ORGANISM: ARTIFICIAL SEQUENCE
<220> FEATURE:
<223> OTHER INFORMATION: IL-2tm2 protein sequence.
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (218)..(218)
<223> OTHER INFORMATION: Xaa can be any naturally occurring amino acid
<220> FEATURE:
<221> NAME/KEY: misc_feature
<222> LOCATION: (221)..(221)
<223> OTHER INFORMATION: Xaa can be any naturally occurring amino acid
<220> FEATURE:
<221> NAME/KEY: misc_feature
<222> LOCATION: (248)..(248)
<223> OTHER INFORMATION: Xaa can be any naturally occurring amino acid
<220> FEATURE:
<221> NAME/KEY: misc_feature
<222> LOCATION: (255)..(256)
<223> OTHER INFORMATION: Xaa can be any naturally occurring amino acid
<220> FEATURE:
<221> NAME/KEY: misc_feature
<222> LOCATION: (267)..(267)
<223> OTHER INFORMATION: Xaa can be any naturally occurring amino acid
<220> FEATURE:
<221> NAME/KEY: misc_feature
<222> LOCATION: (282)..(282)
<223> OTHER INFORMATION: Xaa can be any naturally occurring amino acid
<220> FEATURE:
<221> NAME/KEY: misc_feature
<222> LOCATION: (293)..(293)
<223> OTHER INFORMATION: Xaa can be any naturally occurring amino acid

<400> SEQUENCE: 12

Gln Leu Ala Ser Val Xaa Thr Xaa Ala Trp Tyr Arg Ala Arg Ile Pro
1               5                   10                  15

Ala Thr Met Ala Pro Thr Ser Ser Thr Lys Lys Thr Gln Leu Gln
            20                  25                  30

Leu Glu His Leu Leu Leu Asp Leu Gln Met Ile Leu Asn Gly Ile Asn
            35                  40                  45

Asn Tyr Lys Asn Pro Lys Leu Thr Arg Met Leu Thr Phe Lys Phe Tyr
        50                  55                  60

Met Pro Lys Lys Ala Thr Glu Leu Lys His Leu Gln Cys Leu Glu Glu
65                  70                  75                  80

Glu Leu Lys Pro Leu Glu Glu Val Leu Asn Leu Ala Gln Ser Lys Asn
                85                  90                  95

Phe His Leu Arg Pro Arg Asp Leu Ile Ser Asn Ile Asn Val Ile Val
            100                 105                 110
```

```
Leu Glu Leu Lys Gly Ser Glu Thr Thr Phe Met Cys Glu Tyr Ala Asp
        115                 120                 125

Glu Thr Ala Thr Ile Val Glu Phe Leu Asn Arg Trp Ile Thr Phe Cys
130                 135                 140

Gln Ser Ile Ser Thr Leu Thr Glu Phe Gly Thr Arg Ala Asp Leu Gln
145                 150                 155                 160

Pro Lys Met Ile Pro Ala Val Val Leu Leu Leu Leu Leu Val Glu
                165                 170                 175

Gln Ala Ala Leu Gly Glu Pro Gln Leu Cys Tyr Ile Leu Asp Ala
                180                 185                 190

Ile Leu Phe Leu Tyr Gly Ile Val Leu Thr Leu Leu Tyr Cys Arg Asp
        195                 200                 205

Asp Pro Leu Glu Ser Arg Gly Pro Val Xaa Thr Arg Xaa Ser Ala Ser
    210                 215                 220

Thr Val Pro Ser Ser Cys Gln Pro Ser Val Val Cys Pro Ser Pro Val
225                 230                 235                 240

Pro Ser Leu Thr Leu Glu Gly Xaa Thr Pro Thr Val Leu Ser Xaa Xaa
                245                 250                 255

Asn Glu Glu Ile Ala Ser His Cys Leu Ser Xaa Cys His Ser Ile Leu
                260                 265                 270

Gly Gly Gly Val Gly Ala Gly Gln Gln Xaa Gly Arg Ile Gly Lys Thr
        275                 280                 285

Ile Ala Gly Met Xaa
        290

<210> SEQ ID NO 13
<211> LENGTH: 934
<212> TYPE: DNA
<213> ORGANISM: Artificial Sequence
<220> FEATURE:
<223> OTHER INFORMATION: Entire IL-2TM sequence.
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (778)..(778)
<223> OTHER INFORMATION: n is a, c, g, or t
<220> FEATURE:
<221> NAME/KEY: misc_feature
<222> LOCATION: (823)..(823)
<223> OTHER INFORMATION: n is a, c, g, or t
<220> FEATURE:
<221> NAME/KEY: misc_feature
<222> LOCATION: (850)..(850)
<223> OTHER INFORMATION: n is a, c, g, or t
<220> FEATURE:
<221> NAME/KEY: misc_feature
<222> LOCATION: (862)..(862)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (884)..(884)
<223> OTHER INFORMATION: n is a, c, g, or t
<220> FEATURE:
<221> NAME/KEY: misc_feature
<222> LOCATION: (916)..(916)
<223> OTHER INFORMATION: n is a, c, g, or t
<220> FEATURE:
<221> NAME/KEY: misc_feature
<222> LOCATION: (919)..(919)
<223> OTHER INFORMATION: n is a, c, g, or t
```

<220> FEATURE:
<221> NAME/KEY: misc_feature
<222> LOCATION: (929)..(929)
<223> OTHER INFORMATION: n is a, c, g, or t

<400> SEQUENCE: 13

```
gctggagctc cccgcggtgg cggccgcccc tggnattaca aggatgacga cgataagagc      60
ccgggcggat ccgcacctac ttcaagttct acaaagaaaa cacagctaca actggagcat     120
ttactgctgg atttacagat gattttgaat ggaattaata attacaagaa tcccaaactc     180
accaggatgc tcacatttaa gttttacatg cccaagaagg ccacagaact gaaacatctt     240
cagtgtctag aagaagaact caaacctctg gaggaagtgc taaatttagc tcaaagcaaa     300
aactttcact taagacccag ggacttaatc agcaatatca cgtaatagt tctggaacta      360
aagggatctg aaacaacatt catgtgtgaa tatgctgatg agacagcaac cattgtagaa     420
tttctgaaca gatggattac cttttgtcaa agcatctcaa cactgactga attcggcacg     480
agggccgatc tccagcccaa gatgattcca gcagtggtct tgctcttact ccttttggtt    540
gaacaagcag cggccctggg agagcctcag ctctgctata tcctggatgc catcctgttt    600
ctgtatggaa ttgtcctcac cctcctctac tgtcgactga gatccaagt gcgaaaggca     660
gctataacca gctatgagaa atcagatggt gtttacacgg gcctgagcac caggaaccag    720
gagacttaca agactctgaa gcatgagaaa ccaccacagt agctttagaa tagatgcngg    780
catattcttc tttggcttct gggtctttca gccctcatgg gtnggcatca catatgcctg    840
catgccattn acaccagctg gncctacccc tataangatc ctgngtccta aattaatata    900
caccaggggg ttcctnctnc ctgttaaana ctac                               934
```

<210> SEQ ID NO 14
<211> LENGTH: 309
<212> TYPE: DNA
<213> ORGANISM: Artificial Sequence
<220> FEATURE:
<223> OTHER INFORMATION: FC receptor alpha transmembrane domain
      sequence from IL-2tm.

<400> SEQUENCE: 14

```
tgaattcggc acgagggccg atctccagcc caagatgatt ccagcagtgg tcttgctctt      60
actccttttg gttgaacaag cagcggcccct gggagagcct cagctctgct atatcctgga    120
tgccatcctg tttctgtatg gaattgtcct caccctcctc tactgtcgac tgaagatcca    180
agtgcgaaag gcagctataa ccagctatga aaatcagat ggtgtttaca cgggcctgag    240
caccaggaac caggagactt acaagactct gaagcatgag aaaccaccac agtagcttta    300
gaatagatg                                                              309
```

<210> SEQ ID NO 15
<211> LENGTH: 880
<212> TYPE: DNA
<213> ORGANISM: Artificial Sequence
<220> FEATURE:
<223> OTHER INFORMATION: IL-2TM2 nucleotide sequence.
<220> FEATURE:
<221> NAME/KEY: misc_feature
<222> LOCATION: (744)..(744)
<223> OTHER INFORMATION: n is a, c, g, or t
<220> FEATURE:
<221> NAME/KEY: misc_feature
<222> LOCATION: (801)..(801)
<223> OTHER INFORMATION: n is a, c, g, or t

```
<220> FEATURE:
<221> NAME/KEY: misc_feature
<222> LOCATION: (845)..(845)
<223> OTHER INFORMATION: n is a, c, g, or t
<220> FEATURE:
<221> NAME/KEY: misc_feature
<222> LOCATION: (878)..(878)
<223> OTHER INFORMATION: n is a, c, g, or t

<400> SEQUENCE: 15
ccagctggct agcgtttaaa cttaagcttg gtaccgagct cggatcccgg ccaccatggc      60
acctacttca agttctacaa agaaaacaca gctacaactg gagcatttac tgctggattt     120
acagatgatt ttgaatggaa ttaataatta caagaatccc aaactcacca ggatgctcac     180
atttaagttt tacatgccca agaaggccac agaactgaaa catcttcagt gtctagaaga     240
agaactcaaa cctctggagg aagtgctaaa tttagctcaa agcaaaaact ttcacttaag     300
acccagggac ttaatcagca atatcaacgt aatagttctg gaactaaagg gatctgaaac     360
aacattcatg tgtgaatatg ctgatgagac agcaaccatt gtagaatttc tgaacagatg     420
gattaccttt tgtcaaagca tctcaacact gactgaattc ggcacgaggg ccgatctcca     480
gcccaagatg attccagcag tggtcttgct cttactcctt ttggttgaac aagcagcggc     540
cctgggagag cctcagctct gctatatcct ggatgccatc ctgtttctgt atggaattgt     600
cctcaccctc ctctactgtc gagatgatcc gctcgagtct agagggcccg tttaaacccg     660
ctgatcagcc tcgactgtgc cttctagttg ccagccatct gttgtttgcc cctcccccgt     720
gccttccttg accctggaag gtgncactcc cactgtcctt tcctaataaa atgaggaaat     780
tgcatcgcat tgtctgagta ngtgtcattc tattctgggg ggtggggtgg gggcaggaca     840 gcaangggggg aggattggga agacaatagc aggcatgnct                          880
```

IL-2 TRANSMEMBRANE CONSTRUCT

CROSS-REFERENCE TO RELATED APPLICATION

This application claims the benefit of U.S. Provisional Application No. 60/452,989, filed Mar. 7, 2003, which application is incorporated by reference.

BACKGROUND OF THE INVENTION

The present invention relates to methods and compositions for use in cancer therapeutic applications. More specifically, the present invention relates to fusion proteins, expression vectors, and cancer treatment methods using fusion proteins according to the invention.

Interleukin 2 ("IL-2) is a cytokine produced primarily by T cell lymphocytes. It is also a compound that has been shown to have anti-tumor effects. Mertelsmann & Welte, *Human interleukin-2 molecular biology, physiology and clinical possibilities.*, Immunobiol. 172: 400-419 (1986). Human IL-2 is a 15-kD glycoprotein composed of 133 amino acids. Eckenburg et al., *The First α Helix of Interleukin (IL)-2 Folds as a Homotetramer, Acts as an Agonist of the IL-2 Receptor β Chain, and Induces Lymphokine-activated Killer Cells. J. Exp. Med.*, 191:529-539 (2000); and Kurzrock, *Cytokine: Interleukins and Their Receptors. Massachusetts: Kluwer Academic Publishers*, 1995; 83-97. Produced primarily by CD4+ helper T cells, the cytokine consists of four anti-parallel alpha helices that are connected by three loops. IL-2 was first described as a T cell growth factor for antigen-activated T cells. Id. IL-2 is necessary for induction of antigen-specific cytotoxic T cells. In addition, this cytokine is a differentiation-maturation factor for B cells and T cells. Herblot, et al. *IL-2-Dependent Expression of Genes Involved in Cytoskeleton Organization, Oncogene Regulation, and Transcriptional Control. J. Immunol.*, 162:3280-3288. (1999). At high concentrations (>600 IU/ml), IL-2 is also the principle cytokine responsible for inducing NK cell-derived lymphokine-activated killer (LAK) cells. Cytotoxic T and NK lymphocytes are believed to be critical for recognition of aberrant or malignant cells and eradication of tumors. Mertelsmann & Welte, *Human interleukin-2 molecular biology, physiology and clinical possibilities.*, Immunobiol. 172: 400-419 (1986); Kurzrock, *Cytokine: Interleukins and Their Receptors. Massachusetts: Kluwer Academic Publishers*, 1995; 83-97; Grimm & Wilson, *The human lymphokine-activated killer system. Purified recombinant interleukin 2 activates cytotoxic lymphocytes which lyse both natural killer-resistant autologous and allogeneic tumors and trinitrophenyl-modified autologous peripheral blood lymphocytes, Cell Immunol.*, 94: 568-578 (1985); Yao L, et al. Contribution of natural killer cells to inhibition of angiogenesis. Blood. 5:1612-1621. (1999); Luo et al., *Comparison of the Effects of Immunosuppressive Factors from Newly Established Colon Carcinoma Cell Cultures on Human Lymphocyte Proliferation and Cytokine Secretion, Tumor Biol.*, 21:11-20. (2000); Schneeberger, et al., *The Tumorigenicity of IL-2 Gene-Transfected Murine M-3D Melanoma Cells Is Determined by the Magnitude and Quality of the Host Defense Reaction: NK Cells Play a Major Role, J. Immunol.*, 162:6650-6657. (1999).

These anti-tumor properties provide the basis for IL-2 therapy of cancer. Gilboa & Lyerly, *Biologic therapy of cancer updates*, Vol. 4:6 (1994). Intravenous administration of recombinant human IL-2 is FDA-approved for use in the treatment of advanced melanoma and renal cell carcinoma. Kurzrock, *Cytokine: Interleukins and Their Receptors. Massachusetts: Kluwer Academic Publishers*, 83-97. (1995). IL-2 immunotherapy produces responses in about 15% of melanoma patients and 20% in renal cell carcinoma patients. Fisher et al., *High-dose aldesleukin in renal cell carcinoma: Long term survival update, Cancer J.*, 3: S70-S72 (1997). Interestingly, 5-10% of patients that respond to IL-2 immunotherapy experience a durable complete response with up to 15 years follow up. Legha, *Durable complete responses in metastatic melanoma treated with interleukin-2 in combination with interferon alpha and chemotherapy, Semin. Oncol.*, 24: S39-S43, (1997). However, IL-2 therapy produces severe dose-dependent toxicity that often prevents the patient from completing the IL-2 treatment regimen. Siegel & Puri, *Interleukin-2 toxicity, J. Clin. Oncol.*, 9: 694-704 (1991). Common specific side effects of the therapy include weight gain, ascites, dyspnea, pulmonary edema and severe hypotension.

Efforts to circumvent these side effects have led to IL-2-based gene therapy protocols. Gilboa & Lyerly, *Biologic therapy of cancer updates*, Vol. 4:6 (1994). In some of these protocols, tumor cells were engineered to secrete IL-2 into the microenvironment surrounding the tumor. Most tumors contain infiltrating CD8+ lymphocytes. Topalian et al., *Tumor-specific cytolysis by lymphocytes infiltrating human melanomas, J. Immunol.*, 142:3714. (1989), Rosenburg et al., *Use of tumor infiltrating lymphocytes and interleukin-2 in the immunotherapy of patients with metastatic melanoma, N. Engl. J. Med.*, 319:1676. When these cells are initially isolated from tumors, they can be activated and clonally expanded in the presence of IL-2 to generate tumor-specific cytotoxic lymphocytes. Thus, a goal of gene therapy is to cause intratumoral secretion of activating cytokines resulting in enhanced activation of cytotoxic tumor-infiltrating lymphocytes (TIL) within tumors. Emtage et al., *A double recombinant adenovirus expressing the costimulatory molecule B7-1 (murine) and human IL-2 induces complete tumor regression in a murine breast adenocarcinoma model, J. Immuno.*, 160: 2531-2538 (1998).

Examples of successful IL-2 based gene therapy have been published. Rochlitz et al., *Gene Therapy Study of Cytokine-Transfected Xenogeneic Cells (Vero-interleukin-2) in Patients with Metastatic Solid Tumors, Cancer Gene Therapy*, 6:271-281, (1999). Horton et al. evaluated IL-2 gene therapy of murine ovarian cancer. Horton et al., *IL-2 plasmid therapy of murine ovarian carcinoma inhibits the growth of tumor ascites and alters its cytokine profile, J. Immunol.*, 163:6378-6385 (1999). Murine ovarian tumors (MOT) were treated with an IL-2 plasmid DNA complexed with the cationic lipid, N-(2-hydroxyethyl)-N,N-dimethyl-2-3-bis(tetradecyloxy)-1-propanaminium bromide/dioleoylphosphatidylethanol-amine (DMRIE/DOPE). MOT tumor-bearing mice injected intraperitoneally with IL-2 plasmid:DMRIE/DOPE on days 5, 8, and 11 after tumor cell implantation demonstrated a significant inhibition of tumor ascites as well as a significant increase in survival. By day 26 after tumor cell injection, 10% of the mice treated with the control pCMV-neo DNA were still alive compared with 70% of the mice treated with IL-2tm:DMRIE/DOPE. Furthermore, the peritoneal fluid of mice treated with IL-2 containing vector: DMRIE/DOPE had an IL-2 specific increase in the levels of IFN-γ and GM-CSF.

Horton et al. also investigated the nature of the immune response to the MOT cells, using nude mice (immunodeficient mice without a thymus and without T cells). Only a modest inhibition of tumor growth occurred in nude mice. This helped to show that T cells are required for IL-2 gene-mediated anti-tumor effects. Horton et al., *IL-2 plasmid*

*therapy of murine ovarian carcinoma inhibits the growth of tumor ascites and alters its cytokine profile, J. Immunol.*, 163:6378-6385 (1999).

These added studies and methods further demonstrate the utility and potential safety of IL-2-based therapies. It would thus be a benefit in the art to provide an alternate method for concentrating cytokines in a tumor to initiate an immune response and attack on the tumor. It would be a further benefit in the art to provide methods for concentrating IL-2 in a tumor to initiate an immune response.

BRIEF SUMMARY OF THE INVENTION

The method of the present invention has been developed in response to the present state of the art, and in particular, in response to the problems and needs in the art that have not yet been fully solved by currently available gene therapy constructs and methods of their use. Thus, the present invention provides compounds and methods for conducting gene therapy in cancer applications using genetic constructs capable of producing a protein comprising a cytokine and the transmembrane domain of another protein. More specifically, the invention provides compounds and methods for conducting gene therapy in cancer applications using genetic constructs capable of producing a protein comprising a cytokine and the transmembrane domain of another protein.

Thus, the present invention provides an approach to gene therapy using a novel fusion gene consisting of a cytokine plus a transmembrane domain. When expressed, the fusion gene produces a membrane-bound cytokine such as an IL-2 protein which may be displayed on the surface of mammalian tumor cells. Thus, the invention further provides membrane-bound IL-2 proteins for use in cancer therapies. Such cell membrane-expressed cytokines may be able to activate immune cells in close proximity to tumor antigens that act to create a specific immune recognition. In other embodiments of the invention, cytokines such as interleukins, interferons, lymphokines, and tumor necrosis factors are substituted into the place of IL-2. Thus, the invention provides a family of proteins comprising a regulatory protein such as a cytokine or a hormone attached to the transmembrane domain of another protein. The invention further includes methods for the use of these compounds, including methods of activating tumor infiltrating lymphocytes in close proximity to cancer or tumor cells.

In methods of the invention incorporating the fusion gene into a plasmid which may be inserted into a cell, the low level of cytokine expression created by the expression of the plasmid encoding the membrane-bound cytokine, such as the IL-2 protein, remains localized to the tumor. As a result, use of the plasmid and the membrane-bound IL-2 protein is not associated with the toxicity previously observed in therapies involving high systemic doses of the cytokine. Marr et al., *Tumour immunotherapy using an adenoviral vector expressing a membrane-bound mutant of murine TNFα, Gene Therapy*, 4:1181-1188 (1997); El-Shami et al., *Induction of antitumor immunity with modified autologous cells expressing membrane-bound murine cytokines, Interferon and Cytokine Res.*, 19:1391-1401 (1999).

According to the invention, a plasmid was engineered and evaluated which contains a transgene encoding membrane bound IL-2 (IL-2tm) insert. Without being limited to any one theory, it is believed that by inducing expression of IL-2 on the surface of tumor cells, IL-2 will activate tumor infiltrating lymphocytes in close proximity to tumor antigens. This activation is thought to increase activation of antigen-specific T cells, and thus to result in destruction of tumor cells expressing tumor-associated antigens. One such IL-2tm construct within the scope of the invention was created by joining the gene for human IL-2 with the transmembrane domain Fcε-γ. Studies investigating the efficacy of a tumor vaccine including inactivated cells "transfected with two plasmid vectors encoding a mutant membrane-bound murine granulocyte-macrophage colony-stimulating factor (MuGM-CSF) and murine interferon γ (MuIFN-γ). El-Shami et al., *Induction of antitumor immunity with modified autologous cells expressing membrane-bound murine cytokines, Interferon and Cytokine Res.*, 19:1391-1401 (1999).

The invention also provides another plasmid including a truncated transmembrane domain and other improvements to potentially improve expression of the vector once transfected into a host cell.

Thus, the invention provides methods for producing membrane-bound cytokines for use in the treatment of cancers and other conditions in which it is desirable to target a cell for destruction by the immune system. The invention further provides plasmids engineered to express membrane-bound regulatory hormones or cytokines on the surface of mammalian tumor cells. In some specific embodiments, the invention provides membrane-bound IL-2 proteins expressed on the surface of mammalian tumor cells resulting from the expression of plasmids of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 3 shows a nucleotide sequence encoding hIL-2 (SEQ ID NO: 1); with bold, underlined text indicating the beginning and end of the hIL-2 gene, including the TAATTAA (SEQ ID NO: 4) stop codon which is later removed by PCR-directed mutagenesis;

FIG. 5 shows the sequence (SEQ ID NO: 2) of the hIL-2+ Fcε-γ fusion gene construct ("IL-2tm") comprising the hIL-2 gene ligated upstream and in frame with the transmembrane domain Fcε-γ derived from the plasmid HTAAA91;

FIG. 6 shows the sequence of the IL-2tm construct ligated in the proper reading frame into the pCMV2b mammalian expression vector (SEQ ID NO: 3);

FIG. 9A is a laser confocal micrograph of RD995 cells transfected with pCMV2b vectors containing the IL-2tm construct showing red staining of transfected cells, demonstrating the surface membrane expression of IL-2tm;

FIG. 9B is a laser confocal micrograph of RD995 cells transfected with empty pCMV2b vectors showing no staining, demonstrating no expression of hIL-2;

FIG. 10A is a laser confocal micrograph of FLAG-stained RD995 cells transfected with pCMV2b vectors or IL-2tm with green staining indicating FLAG antigen expression;

FIG. 10B is a laser confocal micrograph of FLAG-stained RD995 cells transfected with pCMV2b vectors or IL-2tm not showing green staining, and thus indicating no FLAG antigen expression;

FIG. 14 is the sequence of the entire IL-2TM vector of the invention (SEQ ID NO: 11), including nucleotide sequences encoding human IL-2tm and a membrane-bound portion of the FC receptor;

FIG. 15 is the sequence of the FC receptor alpha chain (transmembrane domain sequence) SEQ ID NO: 14, used in IL-2tm;

FIG. 16 is the sequence of the IL-2tm protein encoded by the IL-2TM vector of the invention, SEQ ID NO: 13;

FIG. 18 includes a diagram of the pcDNA3.1 (+/−) vector used to create the IL-2TM2 vector of the invention and its components;

FIG. 20 is the sequence of the IL-2tm2 protein encoded by the IL-2TM2 vector of the invention;

FIG. 21 illustrates the homology between the IL-2tm and IL-2tm2 proteins encoded by the expression vectors of the invention, with the full sequence of the IL-2tm protein shown and the homologous regions shown underlined; and FIG. 22 is the nucleotide sequence used in the IL-2TM2 vector (SEQ ID NO: 15) to encode the IL-2tm2 fusion protein.

DETAILED DESCRIPTION OF THE INVENTION

Figure 1:
FIG. 1 is an image of a gel showing bands of cut hIL-2 and uncut VR 1103 plasmid observed after the plasmid VR1103 was exposed to the restriction enzymes PstI and BamHI used to excise the hIL-2 gene from the plasmid.

The presently preferred embodiments of the present invention will be understood by reference to the drawings and following description. It will be readily understood that the methods, proteins, fusion genes, and plasmids of the present invention, as generally described and illustrated in the figures herein, could be arranged and designed in a wide variety of different configurations. Thus, the following more detailed description of the embodiments of the methods, proteins, fusion genes, and plasmids of the present invention, as represented in FIGS. 1 through 13, is not intended to limit the scope of the invention, as claimed, but is merely representative of presently preferred embodiments of the invention.

The practice of the present invention will employ, unless otherwise indicated, conventional methods of virology, microbiology, molecular biology, and recombinant DNA techniques within the skill of the art. Such techniques are fully explained in the literature. See, e.g., Sambrook, et al., *Molecular Cloning: A Laboratory Manual (Current Edition)*; *DNA Cloning: A Practical Approach,* vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *CRC Handbook of Parvoviruses,* vol. I & II (P. Tijessen, ed.); *Fundamental Virology, 2nd Edition,* vol. I & II (B. N. Fields & D. M. Knipe, eds.).

All publications, patents and patent applications cited herein, whether supra or infra, are hereby incorporated by reference in their entirety. As used in this specification and the appended claims, the singular forms "a," "and," and "the" include plural references unless the content clearly dictates otherwise.

According to the invention, fusion genes are provided which contain a protein such as a cytokine or a hormone and a transmembrane domain. Some of these fusion genes comprise a cytokine such as an interleukin attached to a transmembrane domain. The term "cytokine" is used herein to describe a family of small proteins involved in communication between cells of the immune system. Members of this family include interleukins, interferons, lymphokines, and tumor necrosis factors. Fusion genes according to the invention may be produced including cytokines such as IL-2, IL-12, IL-15, and γ-interferon. The term "hormone" is used to include substances such as peptides, steroids, and artificial compounds used to affect physiological activity such as growth or metabolism. The invention provides a fusion gene encoding such a protein and the transmembrane domain of another protein.

In some embodiments of the invention, a fusion gene containing human interleukin 2 (hIL-2) and a transmembrane domain (IL-2tm) derived from Fcε-γ is provided which was created using molecular genetic approaches. The term "fusion gene" is used herein to denote a hybrid gene, comprised of parts of two other genes, in this case, selected for their individual properties. A "fusion protein" as used herein, is the product of such a fusion gene, here having separate domains with properties unique to its constituent genes.

Further, as used herein, the terms "IL-2" and "hIL-2" generally refer to human interleukin-2 or to a nucleic acid encoding human interleukin-2, unless noted otherwise. Similarly, the terms "IL-2tm", "hIL-2tm", "IL-2tm2", and "hIL-2tm2" refer to a transmembrane protein product of the genetic constructs of the invention, or to the transmembrane constructs themselves unless noted otherwise. The constructs of the invention provide a transmembrane anchor allowing hIL-2 to be expressed at the cell membrane of transfected cells in close proximity to tumor infiltrating lymphocytes (TIL cells) and tumor specific antigens. El-Shami et al., *Induction of antitumor immunity with modified autologous cells expressing membrane-bound murine cytokines, Interferon and Cytokine Res.,* 19:1391-1401 (1999). According to the invention, the transgene constructs were also cloned into mammalian expression vectors including pCMV2b and pcDNA3.1(+/−). Other suitable expression vectors, including mammalian expression vectors are known to one of ordinary skill in the art, and may be suitable for use in the invention. Similarly, although FLAG tagging proteins are used in one exemplary embodiment of the invention, one of ordinary skill in the art would be aware of many other suitable tagging proteins usable with the vectors, fusion genes, fusion proteins, and methods of the invention.

IL-2tm was transfected into murine RD995 tumor cells. Cells were evaluated for IL-2tm mRNA and protein expression. RT-PCR was performed with DNA based primers that span the IL-2 gene and the Fcε-γ gene and were used to distinguish the transgene from any native IL-2 mRNA (if present). This sequence has no known mammalian homologues. DNase treatment was used to exclude carry over of the IL-2tm containing pCMV2b plasmid. Using this RT-PCR assay, it was found that IL-2tm mRNA was expressed in transfected RD995 tumor cells but not in pCMV2b transfected or parental RD995 cells. Western blot analysis was performed to detect IL-2tm protein in transfected RD995 cells. IL-2tm was detectable in RD995 transfected with IL-2tm (a 27 kD protein). Protein expression persisted for at least 5 days following transfection. Interestingly, two bands of IL-2 were seen on the Western blot. One band correlated with the expected 27 kDa IL-2tm protein. The other band correlated with IL-2 (18 kD), which suggests cleavage of the IL-2tm from the transmembrane anchor. The parental RD995 tumor was shown not to produce any IL-2 protein. Further investigation will be necessary to determine the exact site of cleavage and the enzyme responsible.

IL-2tm protein expression on the surface of cells was confirmed by immunofluorescent staining of IL-2tm transfected RD995 cells. Anti-hIL-2 antiserum staining of RD995 cells transfected with IL-2tm showed that hIL-2 was expressed on the surface membrane by laser confocal microscopy. Anti-FLAG antibody was used to visualize the FLAG neoprotein that had been added to the N-terminus of IL-2tm. Inmunofluorescent staining for FLAG also confirmed expression at the surface of IL-2tm transfected RD995. Parental RD995 or RD995 transfected with pCMV2b (empty expression vector) did not exhibit surface expression of FLAG or IL-2 protein.

To test the biologic activity of the transgene, groups of 10 syngeneic (C3H/HEN) mice were injected with 105, 5×105 or 106 tumor cells. Mice implanted with equivalent numbers of pCMV2b or parental tumors served as controls. Expression of the transgene in IL-2tm transfected RD995 cells was verified at the start of the experiment. Groups of mice implanted with 106 or 5×105 IL-2tm transfected tumor cells grew at a far slower rate than pCMV2b transfected tumor cells or parental RD995 cells. The experiment was terminated on day 40 due to the large size of tumors in control mice. To assess whether the transgene was still expressed, mice were sacrificed and excised tumors were assayed for mRNA expression of IL-2tm or pCMV2b. It was found that mRNA expression had been lost.

A trivial explanation for the decreased proliferation rate of RD995 cells transfected with IL-2tm (in C3H/HEN mice) might be due to nonspecific effects of the transgene. Tritiated thymidine incorporation into transfected and non-transfected tumor cells established that these cells proliferate at essentially at the same rate, thus excluding this possibility.

Biological activity of IL-2tm was analyzed by utilizing an IL-2 dependent cell line. Gillis & Smith, *Long term culture of tumour-specific cytotoxic T cells*, Nature, 268:154-156. (1977); Belani & Weine, *Expression of both B7-1 and CD28 contributes to the IL-2 responsiveness of CTLL-2 cells*, Immunology, 87:271-274. (1994). This assay (with a sensitivity of 17 U IL-2/well) was unable to detect bioactive IL-2 in 105 tumor cells. Without being limited to any one theory, this finding may indicate low levels of IL-2tm expression. These results may alternately reflect the expression of inactive IL-2tm protein. If further experiments determine that the IL-2tm protein is indeed inactive, one potential cause could be conformational issues. Hydrophobicity plots (data not shown) suggest that the residual intracellular domain of Fcε-γ may be folded when expressed at the cell surface along with the IL-2 protein. Without being limited to any one theory, this could potentially sterically hinder IL-2 from interacting with the IL-2 receptor.

The mechanism that resulted in decreased growth of RD995 cells transfected with IL-2tm in C3H/HEN mice may be further investigated. Additional tumor cell lines may be transfected with modified IL-2tm plasmid (modifications described in the previous paragraph) to evaluate growth potential in vivo. Histological studies of tumor infiltrating lymphocytes and studies of tumor-specific T cell activation may be conducted to help evaluate the mechanism of the anti-tumor effect.

Further, investigation of therapies against non-tumor-forming cancers may be investigated by exploring the ability of systemic introduction of expression vectors encoding the therapeutic fusion proteins of the invention to activate immune response to cancer cells, including cancer cells spread throughout a patient's body in a diffuse manner.

The gene construct of the invention may potentially be used in gene therapy of cancer in humans. Activated TIL cells may be able to destroy tumors by recognizing tumor-associated antigens. Furthermore, activated TIL cells may have the ability to migrate throughout a patient's body and destroy tumor metastases. The IL-2tm vector may provide a practical gene therapy reagent for use against human cancer.

Construction of IL-2tm

To test the hypothesis that membrane expression of IL-2 would lead to activation of T-cells infiltrating into cancers, it was necessary to create a fusion gene containing IL-2 and a transmembrane domain. The gene for hIL-2 (plasmid VR1103) was acquired from Vical, Inc. hIL-2 was removed from pVR1103 because the flanking sequences of the hIL-2 gene in the VR1103 vector were unknown. Restriction enzymes PstI and BamHI were used to cut the hIL-2 gene from the plasmid. The gene was isolated on a low melting point 1% agarose gel (FIG. 1). The expected hIL-2 size was 339 bp plus 217 extra base pairs from pVR1103, yielding a total of 616 bp. Referring now to FIG. 1, lane 2 (indicated by an arrow) shows a faint hIL-2 band of 616 base pairs. hIL-2 DNA was then isolated from the 1% agarose gel using the GeneCAPSULE™ method.

Figure 2:
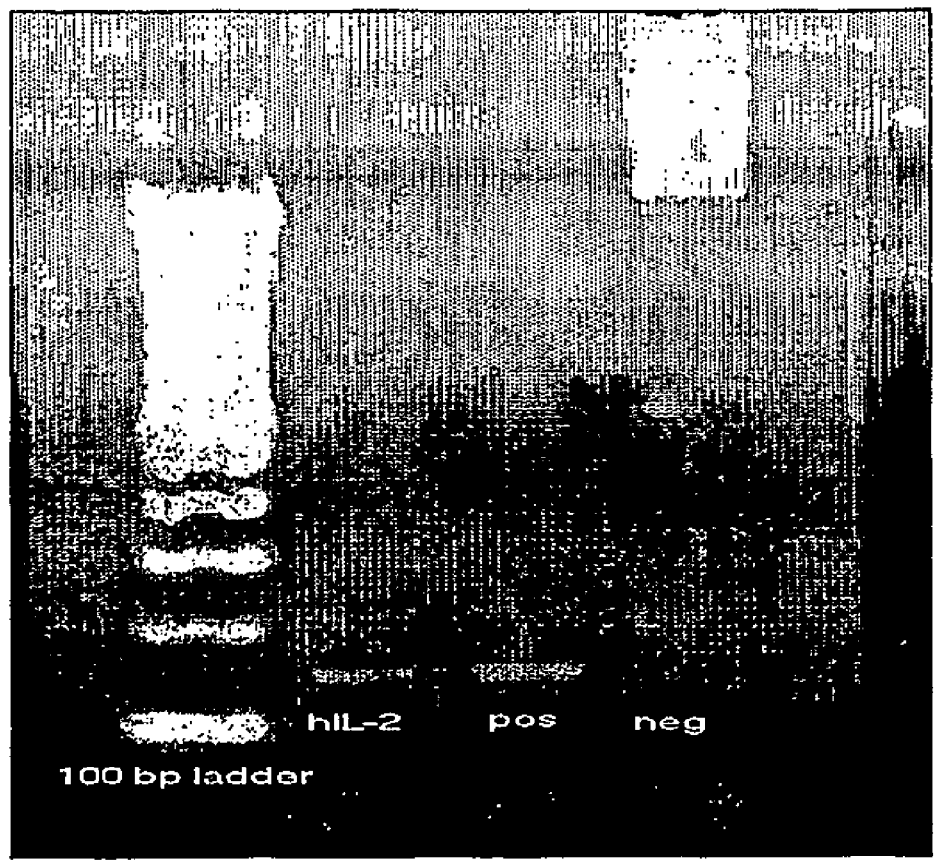
FIG. 2 is an image of a gel showing the results of PCR used to verify DNA insertion of a pBluescript KS cloning vector comprising the hIL-2 gene into DH5α™ Competent cells.

In order to identify the stop codon in hIL-2, hIL-2 was ligated into cloning vector pBluescript KS to facilitate sequencing. pbluescript KS was cut with restriction enzymes PstI and BamHI. The gel isolated hIL-2 band (from FIG. 1) and the gel isolated cut pBluescript KS were ligated together. DNA based primers for hIL-2 were used to perform PCR on the ligated pBluescript KS+hIL-2. FIG. 2 illustrates successful ligation of hIL-2 gene into pBluescript.

Figure 4:
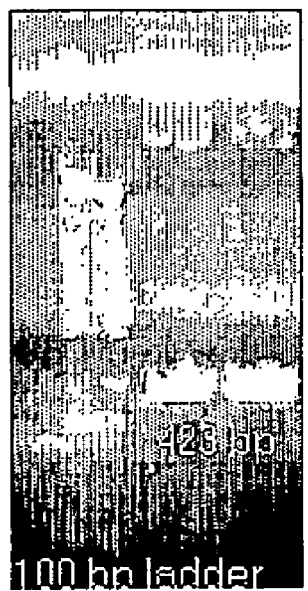
FIG. 4 is an image of a gel showing the PCR-amplified hIL-2 gene modified to lack a stop codon.

Referring now to FIG. 2, hIL-2 was ligated into cloning vector pBluescript KS. DH5α™ Competent cells were transformed with hIL-2/pBluescript KS and screened for recombinant phagemids by lacZ color selection. hIL-2 DNA insertion was then verified by DNA based PCR using primers directed toward hIL-2. PCR was run for 32 cycles resulting in a 155 base pair product. Plasmid VR1103 was used as a positive control and uncut pBluescript KS was used as a negative control.

pBluescript KS was sequenced using T3 promoter-based primers, as shown in FIG. 3 (SEQ ID NO: 1), to identify the stop codon. The bold underlined text present in FIG. 3 indicates the beginning and the end of the hIL-2 gene. The stop codon was removed by PCR directed mutagenesis. DNA based primers were designed to amplify the hIL-2 gene without the stop codon. Restriction sites were also incorporated onto the ends of the primers to maintain proper orientation and reading frame of the hIL-2 gene during ligation. Specifically, primers were designed to incorporate restriction sites BamHI (5' GGA TCC 3') SEQ ID NO: 5, on the sense strand and EcoRI (5' GAA TTC 3') SEQ ID NO: 6, on the antisense strand in order to facilitate insertion of hIL-2 into plasmid HTAAA91 that contains the transmembrane domain Fcε-γ. Herculase™ Enhanced DNA Polymerase was then used to amplify hIL-2 for 30 cycles. The 423 base pair band representing the modified IL-2 gene was isolated from a 1% agarose gel (FIG. 4).

The hIL-2 gene and Fcε-γ transmembrane domain were each cut with BamHI and EcoRI. The hIL-2 (minus the stop codon) construct was ligated upstream and in frame with the transmembrane domain Fcε-γ derived from the plasmid HTAAA91. Fcε-γ is an accessory signaling protein of the Fcε-γ receptor that has a minimal extracellular domain. DNA sequencing of the hIL-2+Fcε-γ using T3 promoter-based primers was conducted to verify that the stop codon was removed, and that hIL-2 (minus the stop codon) was upstream and in frame with the Fcε-γ transmembrane domain (FIG. 5, see SEQ ID NO: 2). In FIG. 6, bold underlined text shows the beginning of hIL-2 and the beginning of the transmembrane domain Fcε-γ (SEQ ID NO: 3).

Lastly, in order to express hIL-2 on the surface of tumors, a mammalian expression vector was selected to deliver the hIL-2+Fcε-γ fusion gene. pCMV2b contains a cytomegalovirus promoter along with neomycin and kanamycin resistance selection markers. Additionally, pCMV2b also includes an N-terminal FLAG® tagging protein. The FLAG protein was included for use in identifying hIL-2 expression on the surface of tumors.

Restriction enzymes ApaI and BamHI were used to cut HTAAA91 and pCMV2b. The IL-2tm (hIL-2+Fcε-γ) construct was then ligated into pCMV2b as previously described. IL-2tm was sequenced to verify proper insertion into the expression vector. DNA sequencing (FIG. 6) demonstrated that IL-2tm was ligated in the proper reading frame into expression vector pCMV2b (SEQ ID NO: 3). In FIG. 6, the upper bold underlined text indicates the initiation start site and the second bold underlined sequence identifies the beginning of the transmembrane domain.

Figure 7:
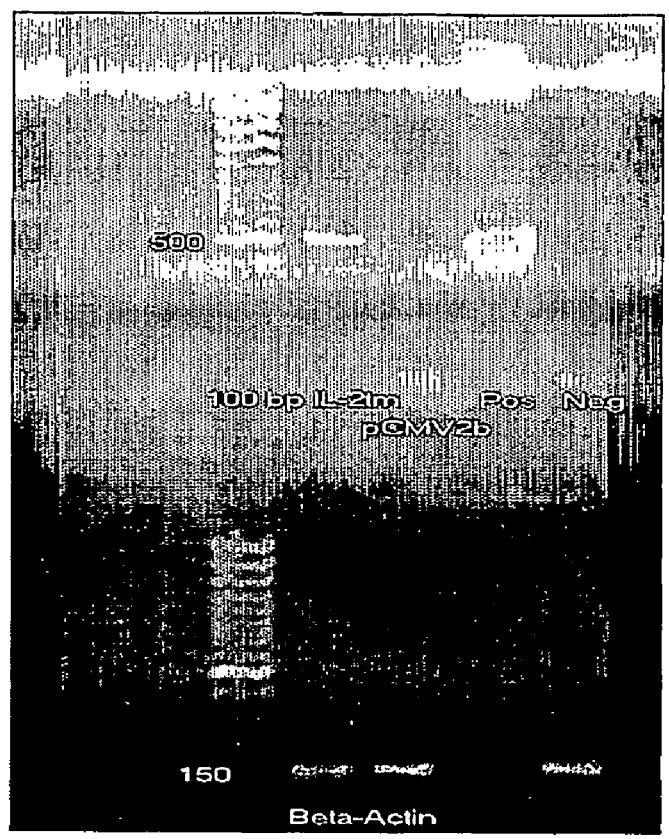
FIG. 7 is an image of a gel showing the IL-2tm mRNA expressed by RD995 cells transfected with pCMV2b vectors containing the IL-2tm construct.
Figure 8:
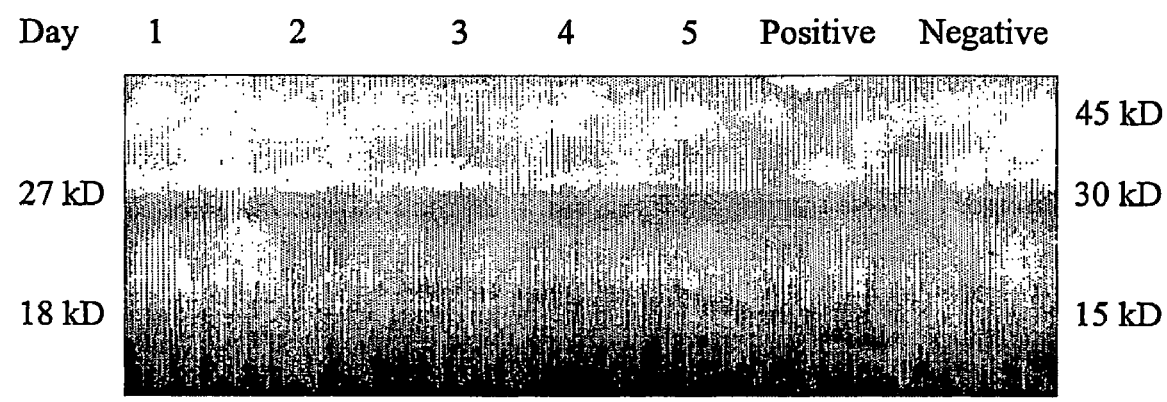
FIG. 8 is a Western blot analysis of IL-2tm expression of RD995 cells transfected with IL-2tm.
Figure 11:
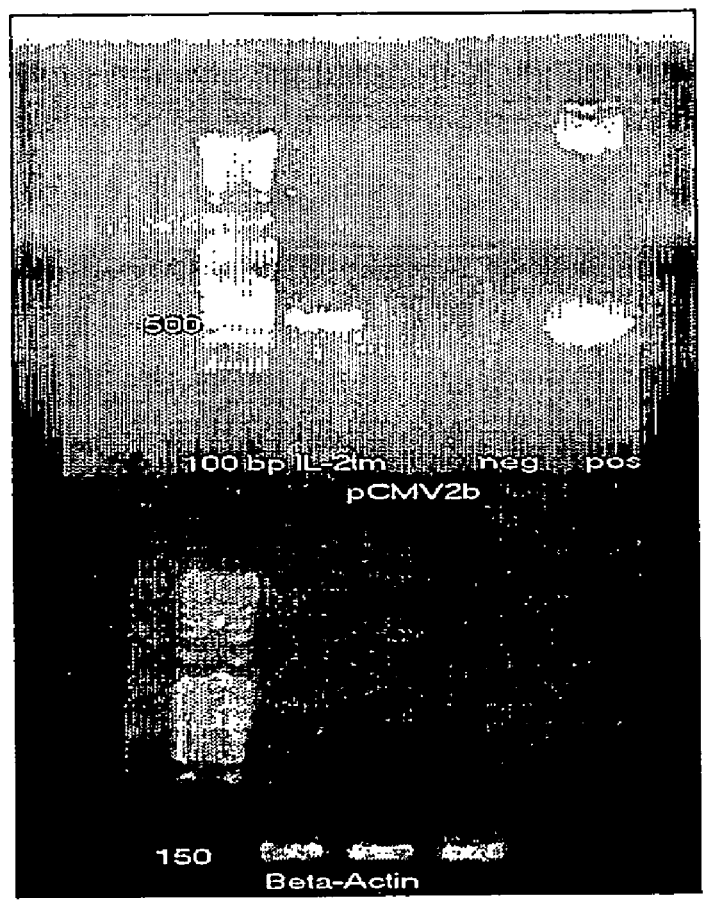
FIG. 11 is an image of a gel showing the results of assays for expression of hIL-2tm mRNA in RD995 tumor cells prior to their introduction into C2H/HEN mice.

Screening for IL-2tm and pCMV2b mRNA and Protein Expression in RD995 Tumor Cells Optimal conditions for transfection of RD995 tumor cells with IL-2tm contained within pCMV2b were next established experimentally. The ability of pCMV2b vector containing IL-2tm to induce mRNA and protein expression was subsequently evaluated. Total RNA was extracted from transfected RD995 tumor cells (2 μg IL-2tm and 10 μl Lipofectin). The RNA was treated with DNase to remove any residual plasmid derived DNA. DNA based primers, spanning the hIL-2+Fcε-γ fusion gene were used to amplify the IL-2tm fusion gene by DNA based PCR. FIG. 7 demonstrates that IL-2tm mRNA was easily detected in transfected RD995 cells. Specifically, in FIG. 7, IL-2tm mRNA expression in RD995 cells transfected with IL-2tm or pCMV2b alone is shown. Total RNA was extracted using TRI-REAGENT and treated with DNase to remove any residual plasmid DNA prior to reverse transcription. Primers were designed to span the hIL-2 gene and the transmembrane domain with an expected 500 base pair PCR product. This gel demonstrates that mRNA expression is present in cells transfected with IL-2tm, but not empty vector (pCMV2b). Control cells transfected with pCMV2b did not express this message.

Expression of IL-2tm protein in transfected RD995 cells was evaluated by Western blot analysis. First, 106 RD995 cells were transfected with IL-2-tm. 106 cells were harvested days 1-5 after transfection and washed in PBS and lysed in RIPA buffer. The lysates were applied to a 12.5% PAGE electrophoresis gel. After electrophoretic transfer to a membrane, and blocking steps, membranes were stained with 1 μg/ml polyclonal rabbit anti-IL-2 antibody. Bands were visualized using Luminol on X-ray film. Recombinant hIL-2 from Chiron was used as a positive control. The positive control shows three expected bands of IL-2 (45 kDa, 30 kDa and 15 kDa) on the right side of blot. Non-transfected RD995 cells were used as a negative control. IL-2tm appears to generate both hIL-2 bound to transmembrane (27 kD) and free hIL-2 (18 kD) on left side of blot. FIG. 9 showed that hIL-2 (18 kD) and hIL-2+transmembrane domain (27 kD) were both present. The native IL-2 produces a band of 15 kDa, but multimeric bands are also seen at 30 kDa and 45 kDa.

Immunofluorescent Antibody Staining for Surface-Bound hIL-2 in RD995 Tumor Cells Laser confocal microscopy was next utilized to demonstrate that IL-2 was being expressed on the surface of transfected RD995 cells. Cells were stained with anti-hIL-2 antiserum and TO-PRO3™ (1 μM/ml) in order to visualize the nucleus. Specifically, RD995 cells transfected with IL-2tm or pCMV2b (106 cells) were stained with anti-hIL-2 or anti-FLAG (FIGS. 9 and 10). TO-PRO3™ nuclear stain applied to the cells after they were stained with anti-hIL-2 or anti-FLAG. In FIG. 9A, red staining of cells transfected with IL-2tm demonstrated surface membrane expression of IL-2. In FIG. 9B, RD995 transfected with empty pCMV2b vector indicates no hIL-2 expression. Untransfected RD995 or RD995 stained with secondary antibody alone were used as negative controls and also showed no staining (data not shown). Referring now to FIG. 10, laser confocal microscopy of FLAG-stained RD995 transfected with IL-2tm or pCMV2b shows green staining in FIG. 10A, demonstrating FLAG antigen expression in RD995 transfected with IL-2tm. In FIG. 10B, however, RD995 transfected with pCMV2b demonstrated no staining.

Evaluation of Growth of RD995 Cells Transfected with IL-2tm in C3H/HEN Mice

It was next hypothesized that expression of IL-2tm protein on tumor cell surface membranes would alter immunologic recognition in mice. The growth of IL-2tm transfected RD995 tumor cells in syngenic mice was evaluated to test this hypothesis. RD995 cells transfected with IL-2tm were implanted subcutaneously into groups of 10 C3H/HEN mice (106, 5×105 or 105 tumor cells per mouse). Mice implanted with equivalent numbers of non-transfected RD995 cells or empty vector (pCMV2b) transfected RD995 cells were used as controls. Prior to subcutaneous implantation of RD995 transfected with IL-2tm or pCMV2b, tumor cells were assayed for mRNA expression of IL-2tm. This was done using primers designed to span the hIL-2 gene and the transmembrane domain. The expected 500 base pair product was generated. The gel shown in FIG. 11 demonstrates that mRNA expression is present, which was absent from parental tumor (neg) and empty vector transfected RD995 (pCMV2b).

Figure 12:
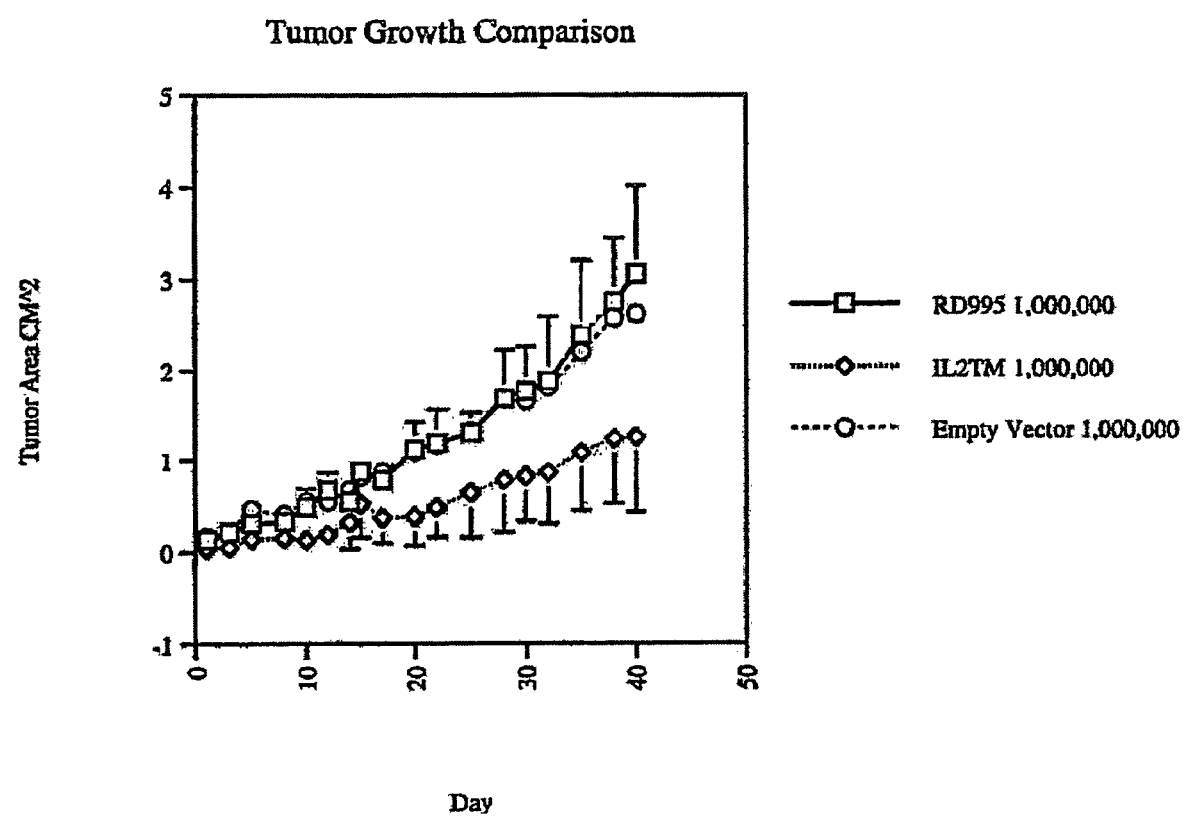
FIG. 12 is a chart comparing the growth of subcutaneous tumors in C3H/HEN mice injected with 106 RD995 cells transfected with IL-2tm, RD995 transfected with pCMV2b (empty vector), or with control RD995 cells.

The maximum cross sectional area of each subcutaneous tumor was measured with calipers every other day. The results are shown in FIG. 12. Growth of IL-2tm transfected tumors was markedly reduced compared to parental or empty vector transfected RD995. The experiment was terminated on day 40 due to excessive size of tumors in control mice. On day 40, tumors in mice implanted with 106 IL-2tm RD995 cells showed reduced growth (52% smaller than in mice bearing pCMV2b RD995 and 59% smaller than parental RD995 tumor cells) (FIG. 12). The group implanted with 5×105 IL-2tm RD995 tumor cells also showed reduced tumor growth (31% smaller tumors than the pCMV2b RD995 group and 30% smaller tumors than the parental RD995 group). No tumors grew in any groups of mice implanted with only 105 cells (data not shown).

On day 40, mice from each group were sacrificed, the tumors excised and assayed for persistence of IL-2tm transgene expression. No residual IL-2tm mRNA could be detected in any tumors harvested on day forty, suggesting IL-2tm was lost prior to this time (data not shown).

Evaluation of the Effect of IL-2tm and pCMV2b or RD995 Proliferation

Figure 13:
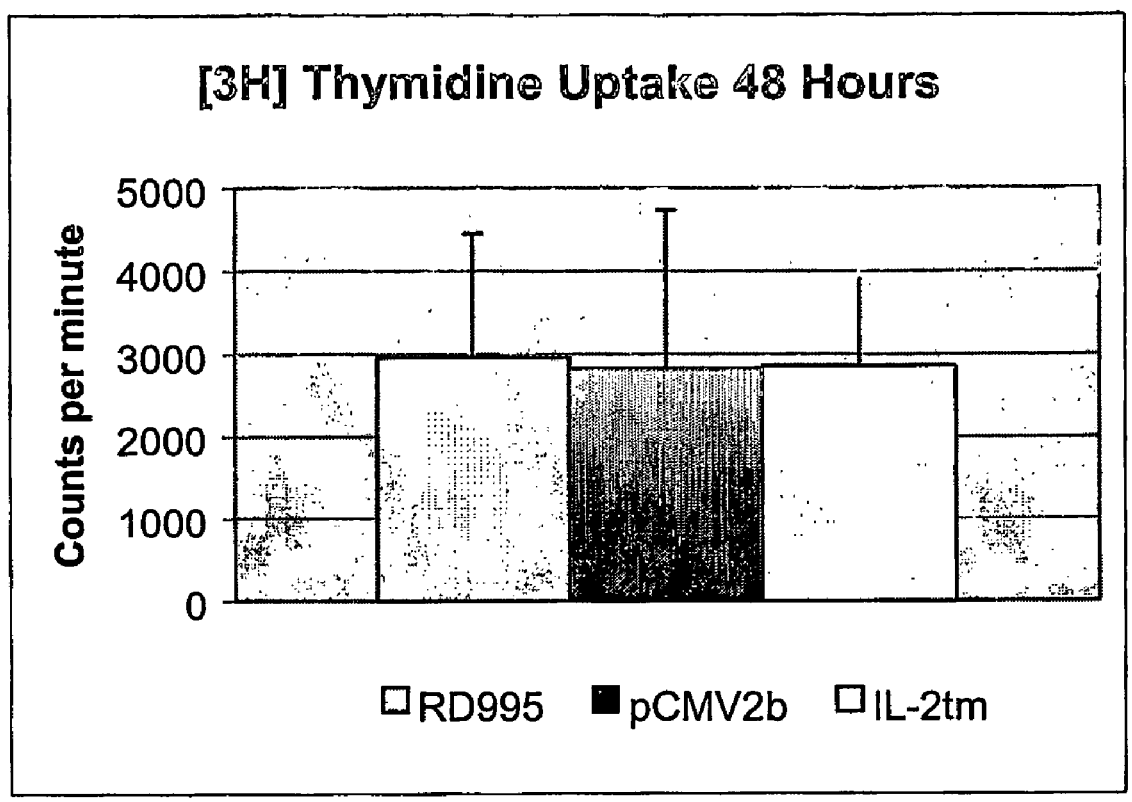
FIG. 13 is a chart noting the thymidine uptake of 105 RD995 cells transfected with IL-2tm, transfected with pCMV2b (empty vector), and with control RD995 cells.

The previous experiment demonstrated that RD995 cells transfected with IL-2tm grow at a slower rate than RD995 transfected with pCMV2b or parental RD995. A trivial explanation for this could be that tumor cells transfected with IL-2tm might have decreased proliferative potential due to some nonspecific cellular effect of the transgene. An in vitro thymidine incorporation assay was used to evaluate this possibility. This experiment showed that RD995 transfected with IL-2tm or pCMV2b had similar thymidine incorporation as nontransfected RD995 (mean plus or minus SD of 24 wells). The results of this experiment measuring thymidine incorporation in 105 RD995, RD995 samples transfected with pCMV2b or IL-2tm after 48 hours in culture are shown in FIG. 13.

Evaluation of Biological Activity of IL-2tm Expressed in Transfected RD995

The biological activity of IL-2tm was analyzed by utilizing a murine cytotoxic T cell line that is dependent on IL-2 for growth. Recombinant human IL-2 is known to result in increased proliferation of CTLL-20 (measured by incorporated [3H]-TdR). Gillis & Smith, *Long term culture of tumour-specific cytotoxic T cells*, Nature, 268:154-156. (1977); Belani & Weine, *Expression of both B7-1 and CD28 contributes to the IL-2 responsiveness of CTLL-2 cells*, Immunology, 87:271-274. (1994).

A standard curve was generated using human recombinant hIL-2. It was found that 17 IU of IL-2 stimulated a measurable proliferation of CTLL-20. The relationship between thymidine incorporation and hIL-2 concentration was almost linear between 17 and 200 IU. This assay showed that RD995 cells transfected with IL-2tm or pCMV2b failed to induce detectable proliferation of CTLL-20. This implies less than 17 IU of biologically active IL-2 was expressed per 105 tumor cells. FIG. 14 provides the sequence coding for the IL-2TM fusion protein with the sequence of the fusion of the Fcε-γ gene in square brackets (SEQ ID NO: 11). The nucleotide sequence coding for the transmembrane domain of the protein is provided alone in FIG. 15. (SEQ ID NO: 14). The nucleotide sequence encoding the IL-2tm fusion protein produced by the IL-2TM expression vector is provided in FIG. 16, SEQ ID NO: 13.

The IL-2TM2 Vector

The IL-2tm vector was next modified to optimize its function and that of the expressed IL-2tm protein. The product of these efforts is the IL-2TM2 vector. In the original vector, IL-2tm was designed to include the FLAG tagging protein to facilitate identification and tracking of the IL-2tm protein. Without being limited to any one theory, it was believed that in some situations, the inclusion of the FLAG sequence in the fusion protein may have altered the tertiary protein structure of the IL-2tm fusion protein. It was also believed that the inclusion of FLAG could also potentially initiate immunological recognition of the IL-2tm protein in future multi-injection experiments. The FLAG sequence was therefore removed from the fusion gene in order to prevent such potential difficulties.

Figure 17:
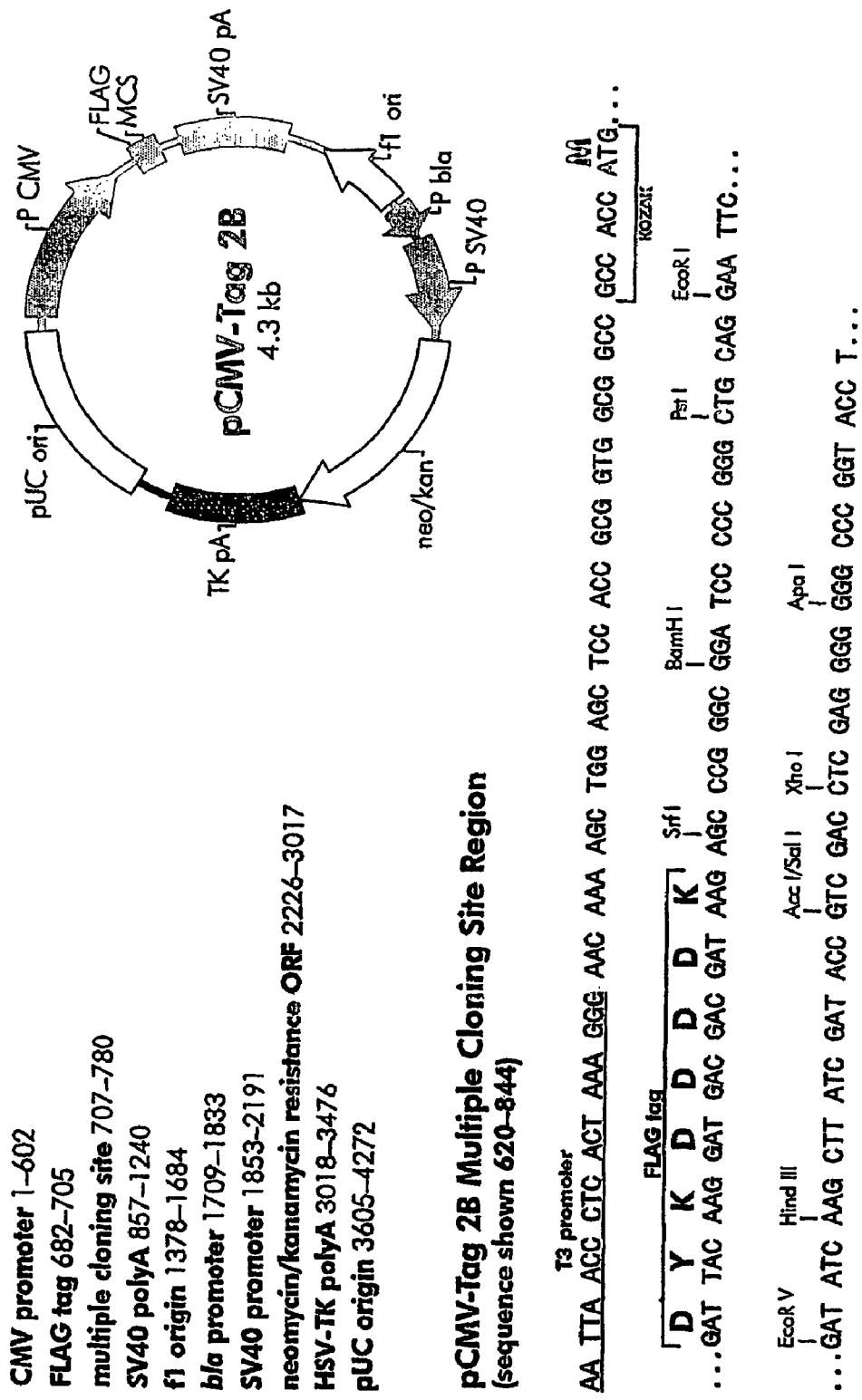
FIG. 17 includes a diagram of the pCMV2b vector used to create the IL-2TM vector of the invention and its components.

It was also noted that the IL-2TM expression vector contained extraneous amino acids that were part of the multiple cloning site in the expression vector. These were removed in order optimize potential function of the expression vector. In addition, it was noted that the mammalian expression vector pCMV2b, used to create IL-2TM, does not contain an enhancer. See, e.g., FIG. 17 and Vile et al., *Cancer therapy: hard lessons and new courses*, Gene Therapy, 7: 2-8. (2000); Li & Haung, *Nonviral gene therapy: promises and challenges*, Gene Therapy, 7:31-34. (2000). It is known in the art that mRNA expression levels may be greatly increased by using an expression vector that includes an enhancer in addition to a promoter. As a result, the IL-2TM2 vector was designed using the pcDNA3.1(+/−) expression vector. See, e.g., FIGS. 18-19. The effects of these design changes was evaluated using the methods used above to assess the effectiveness of the IL-2TM2 vector and the IL-2tm2 fusion protein.

Construction of IL-2TM2

As above, a fusion gene containing IL-2 and a transmembrane domain was created. As before, the gene for hIL-2 (plasmid VR1103) was acquired from Vical, Inc. hIL-2 was removed from pVR1103 because the flanking sequences of the hIL-2 gene in the VR1103 vector were unknown. Restriction enzymes PstI and BamHI were used to cut the hIL-2 gene from the plasmid. The gene was isolated on a low melting point 1% agarose gel (FIG. 1). The expected hIL-2 size was 339 bp plus 217 extra base pairs from pVR1103, yielding a total of 616 bp. Referring now to FIG. 1, lane 2 (indicated by an arrow) shows a faint hIL-2 band of 616 base pairs. hIL-2 DNA was then isolated from the 1% agarose gel using the GeneCAPSULE™ method.

In order to identify the stop codon in hIL-2, hIL-2 was ligated into cloning vector pBluescript KS to facilitate sequencing. pBluescript KS was cut with restriction enzymes PstI and BamHI. The gel isolated hIL-2 band (from FIG. 1) and the gel isolated cut pBluescript KS were ligated together. DNA based primers for hIL-2 were used to perform PCR on the ligated pBluescript KS+hIL-2. FIG. 2 illustrates successful ligation of hIL-2 gene into pBluescript.

Referring now to FIG. 2, hIL-2 was ligated into cloning vector pBluescript KS. DH5α™ Competent cells were transformed with hIL-2/pBluescript KS and screened for recombinant phagemids by lacZ color selection. hIL-2 DNA insertion was then verified by DNA based PCR using primers directed toward hIL-2. PCR was run for 32 cycles resulting in a 155 base pair product. Plasmid VR1103 was used as a positive control and uncut pBluescript KS was used as a negative control.

pBluescript KS was sequenced using T3 promoter-based primers, as shown in FIG. 3 (SEQ ID NO: 1), to identify the stop codon. The bold underlined text in FIG. 3 indicates the beginning and the end of the hIL-2 gene. The stop codon was removed by PCR directed mutagenesis. DNA based primers were designed to amplify the hIL-2 gene without the stop codon. Restriction sites were also incorporated onto the ends of the primers to maintain proper orientation and reading frame of the hIL-2 gene during ligation. Specifically, primers were designed to incorporate restriction sites BamHI (5' GGA TCC 3') SEQ ID NO: 5, on the sense strand and EcoRI (5' GAA TTC 3') SEQ ID NO: 6, on the antisense strand in order to facilitate insertion of hIL-2 into plasmid HTAAA91 that contains the transmembrane domain Fcε-γ. Herculase™ Enhanced DNA Polymerase was then used to amplify hIL-2 for 30 cycles. The 423 base pair band representing the modified IL-2 gene was isolated from a 1% agarose gel (FIG. 4).

The hIL-2 gene and Fcε-γ transmembrane domain were each cut with BamHI and EcoRI. The hIL-2 (minus the stop codon) construct was ligated upstream and in frame with the transmembrane domain Fcε-γ derived from the plasmid HTAAA91. Fcε-γ is an accessory signaling protein of the Fcε-γ receptor that has a minimal extracellular domain. DNA sequencing of the hIL-2+Fcε-γ using T3 promoter-based primers was conducted to verify that the stop codon was removed, and that hIL-2 (minus the stop codon) was upstream and in frame with the Fcε-γ transmembrane domain (see FIG. 5, SEQ ID NO: 2). In FIG. 6, bold underlined text indicates the start of hIL-2 and the beginning of the transmembrane domain Fcε-γ (SEQ ID NO: 3).

Lastly, in order to express hIL-2 on the surface of tumors, a mammalian expression vector was selected to deliver the hIL-2+Fcε-γ fusion gene. pcDNA3.1(+/−) includes a cytomegalovirus promoter along with an enhancer and neomycin and ampicillin resistance selection markers. See FIGS. 18-19.

Figure 19:
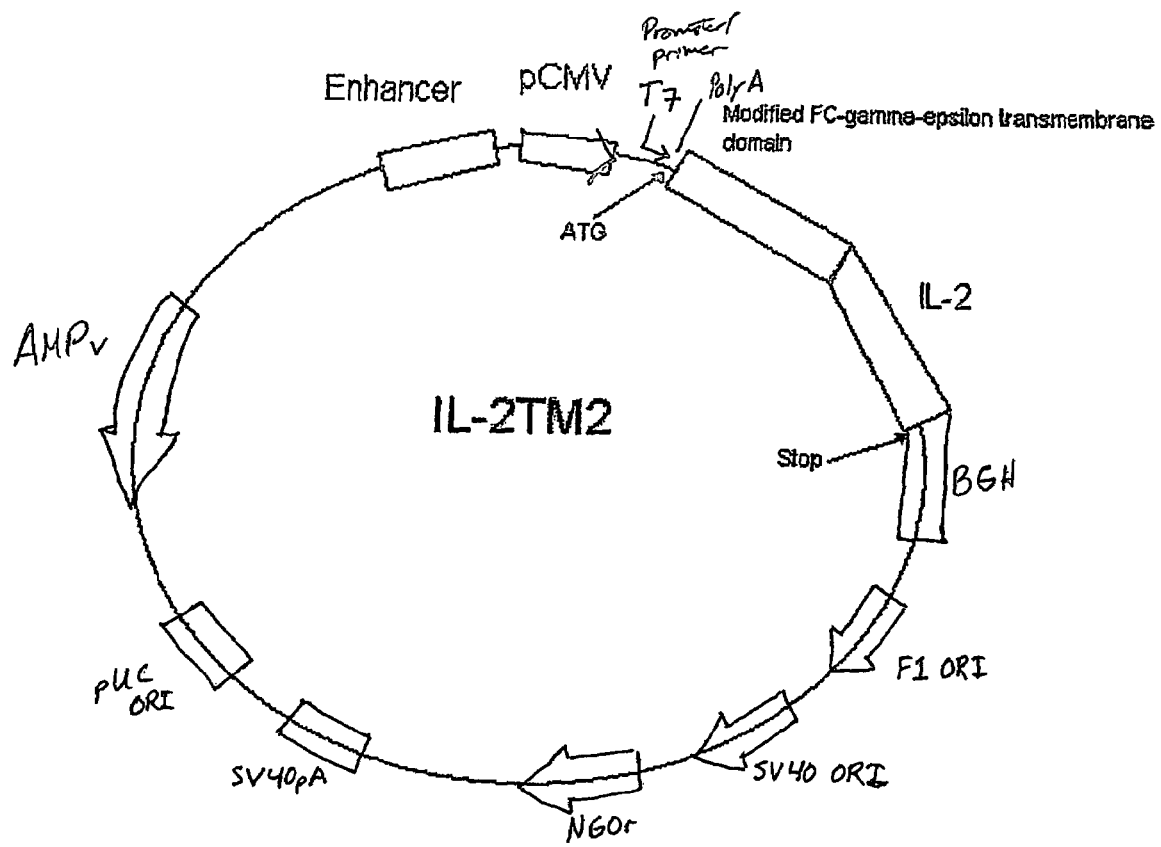
FIG. 19 is a diagram of the IL-2TM2 vector of the invention.

The N-terminal FLAG® tagging protein was removed by PCR-driven mutagenesis. In addition, the Fcε-γ portion of the construct was truncated to include only one transmembrane domain. Without being limited to any one theory, it is believed that these modifications aid the expression efficiency of the construct. Finally, the pcDNA3.1(+/−) vector was itself modified to remove extraneous nucleotides from the multiple cloning site of the vector. FIG. 19.

The IL-2tm2 (hIL-2+Fcε-γ) construct was then ligated into the modified pcDNA3.1(+/−) expression vector as described above. The resulting IL-2TM2 expression vector was sequenced to verify proper insertion into the expression vector. DNA sequencing demonstrated that the sequence encoding IL-2tm2 was ligated into the vector in the proper reading frame. The sequence of the IL-2tm2 protein sequence encoded by the IL-2TM2 vector is provided in FIG. 20 (SEQ ID NO: 12). The homology of the IL-2tm and IL-2tm2 proteins is illustrated in FIG. 21, with the homologous sequences shown underlined. Finally, FIG. 22 is the nucleotide sequence used to encode the IL-2tm2 fusion protein (SEQ ID NO: 15) in the IL-2TM2 construct.

MATERIALS AND METHODS

Insertion of Human Interleukin 2 into Cloning Vector pBluescript KS and Sequence Verification Plasmid VR1103 containing the human Interleukin 2 (hIL-2) gene was obtained from Vical, Inc. Restriction enzymes PstI and BamHI (Life Technologies, Gaithersburg, Md.) were used to excise the hIL-2 gene from the plasmid. The cut VR1103 plasmid was run on a low melting point 1% agarose gel (Sigma Chemical Company, St. Louis, Mo.) and the band containing the IL-2 gene was identified and isolated from the gel using GeneCAPSULE™ (Geno Technology, Inc., St. Louis, Mo.). The expected DNA size was 616 base pairs. The identity of the gene was confirmed by direct DNA sequencing (Huntsman Cancer Institute Core Facility, University of Utah, Salt Lake City, Utah).

Cloning vector pBluescript II KS (+/−) (Stratagene, La Jolla, Calif.) was cut with PstI and BamHI (Life Technologies, Gaithersburg, Md.) and run on a low melting point 1% agarose gel (Sigma Chemical Company, St. Louis, Mo.). pBluescript KS was isolated from the gel to remove the segment of DNA between PstI and BamHI (the stuffer portion). hIL-2 was then ligated into pBluescript KS, by combining 0.5 units of T4 DNA Ligase (Boehringer Mannheim, GmbH, Germany), 5 µl hIL-2 gene (23 ng/µl) insert with 2 µl of cut pBluescript KS (150 ng/µl). DH5α™ Competent Cells (Life Technologies, Gaithersburg, Md.) were transformed with the ligated cloning vector following the protocol in the package insert. Transformed DH5α™ E. coli was plated on ampicillin agar plates (100 µg/ml) for isolation. Selection of bacterial colonies expressing hIL-2 was performed using lacZ color selection of recombinant phagemids. Sterile toothpicks were used to select individual white colonies. The colonies were then grown in LB media with ampicillin (100 µg/ml) for 16 h. A Qiagen™ Plasmid Midi kit (Valencia, Calif.) was used to isolate hIL-2/pBluescript KS. The insertion of intact hIL-2 gene was verified by DNA based PCR, using the primers (5' TGC TGG ATT TAC AGA TGA TTT 3') SEQ ID NO: 7, and (5' CAC TTC CTC CAG AGG TTT G 3'), SEQ ID NO: 8. PCR was run for 32 cycles at 55° C. annealing for 15 sec, 72° C. extension for 30 sec resulting in a 155 base pair product, which was verified by direct sequencing.

Removal of Stop Codon Using PCR Directed Mutagenesis

The stop codon in the IL-2 gene was identified. Primers were designed to remove this stop codon and add restriction sites BamHI (5' GGA TCC 3') SEQ ID NO: 5, on the sense strand and EcoRI (5' GAA TTC 3') SEQ ID NO: 6, on the antisense strand in order to facilitate insertion into a mammalian expression vector. The following primers were used (sense 5' AGA ACT AGT GGA TCC GCA CCT ACT TCA AGT TCT 3') SEQ ID NO: 9, and (antisense 5' GTC AGG GAA TTC AGT CAG TGT TGA GAT GCT TTG 3') SEQ ID NO: 10. PCR of hIL-2/pBluescript KS was performed using the following parameters: 30 cycles at 60° C. annealing for 30 sec, 72° C. extension for 120 sec, using Herculase™ Enhanced DNA Polymerase (Stratagene, La Jolla, Calif.). The resulting 423 bp PCR product was isolated from a 1% agarose gel as described above. Restriction enzymes BamHI and EcoRI were then used to digest the isolated hIL-2 gene. The digested hIL-2 PCR product was separated on a 1% agarose gel and isolated as previously described.

Construction of a hIL-2 Fusion Gene Containing a Transmembrane Domain of Fcε-γ

Fcε-γ was chosen to donate a transmembrane domain based on a previously published study by El-Shami.11 HTAAA91 plasmid encoding Fcε-γ was purchased from ATCC (Manassas, Va.). The Fcε-γ gene was excised from the plasmid using restriction enzymes BamHI and EcoRI. Ligation of Fcε-γ and modified hIL-2 was performed under the following conditions: 0.5 units of T4 DNA Ligase (Boehringer Mannheim, GmbH, Germany), 5 µl of gel extracted Fcε-γ, 2 µl of hIL-2 gene and 8 µl of DEPC treated water. DH5α™ Competent Cells were transformed with the ligation product and grown on ampicillin agar selection plates. The colonies were screened by PCR using primers spanning the fusion product of the IL-2 gene and the transmembrane region of Fcε-γ (5' TGC TGG ATT TAC AGA TGA TTT 3') SEQ ID NO: 7, and (5' CAC TTC CTC CAG AGG TTT G 3') SEQ ID NO: 8. PCR conditions were 32 cycles at 55° C. annealing for 15 sec, 72° C. extension for 30 sec. The PCR products were run on a 1% agarose gel and colonies containing hIL-2/Fcε-γ (IL-2tm) fusion product were chosen for expansion and grown overnight in LB ampicillin broth and isolated with the Qiagen™ Plasmid Midi kit (Valencia, Calif.). The plasmids were sequenced using PCR based sequencing to verify proper insertion of hIL-2 and to ensure removal of the stop codon.

Ligation of hIL-2/Fcε-γ Fusion Gene into the Mammalian Expression Vector pCMV2b

The pCMV2b (Stratagene, La Jolla, Calif.) expression vector was selected to maintain in frame transcription of the hIL-2/Fcε-γ gene. This vector contains a cytomegalovirus promoter along with neomycin and kanamycin resistance selection markers. pCMV2b is an N-terminal FLAG® tagging vector. The FLAG® protein was included to facilitate tracking of the fusion protein, using a FLAG specific antibody.

pCMV2b vector and hIL-2/Fcε-γ were cut with ApaI and BamHI (Life Technologies, Gaithersburg, Md.) and gel isolated as previously described. Ligation of the vector and gene was performed under the following conditions: 1 unit of T4 DNA Ligase (Boehringer Mannheim, GmbH, Germany), 2 µl of ligation buffer (provided in kit), 14 µl of ApaI and BamHI cut pCMV2b, 2 µl of ApaI and BamHI cut hIL-2/Fcε-γ and 3 µl of DEPC treated water. DH5α™ Competent Cells (Life Technologies, Gaithersburg, Md.) were transformed with the resulting plasmid and grown on agar plates containing 50 µg/ml kanamycin. The colonies were screened using the same screening procedure described previously. Lane 2 was isolated from the gel and sequenced using T3 and T7 based primers to verify proper insertion of hIL-2/Fcε-γ into the expression vector pCMV2b. pCMV2b+hIL-2/Fcε-γ is designated the IL-2tm vector.

Transfection of IL-2tm and pCMV2b into Murine Tumor Cells RD995

RD995 was cultured in six-well plates at a concentration of 105 cells per well and allowed to adhere overnight. In order to determine the optimum Lipofectin and DNA concentrations, Lipofectin (1 mg/ml) (Life Technologies, Gaithersburg, Md.) was used to transfect RD995 at the following volumes: 2 µl, 10 µl, and 20 µl along with either 1.0 µg or 2.0 µg of IL-2tm using the procedure described in the Lipofectin package insert. Cells transfected with pCMV2b empty vector served as a control. Optimum Lipofectin/DNA concentration was determined based on the number of RD995 surviving selection with 800 µg/ml G418 (Sigma Chemical Company, ST. Louis, Mo.).

Screening for IL-2tm and pCMV2b mRNA Expression

Using predetermined optimal conditions, RD995 cells were transfected with IL-2tm (2 µg) or pCMV2b empty vector (Lipofectin 10 µl) and allowed to grow for one week. They were then transferred to 200 ml culture flasks (Corning Costar Corporation, Cambridge, Mass.) containing 30 ml of RPMI-1640 (BioWhittaker, Walkersville, Md.) culture media supplemented with 5% fetal calf serum.

After expanding RD995 cultures for one week, 800 µg/ml G418 (Sigma Chemical Company, ST. Louis, Mo.) was added to cultures to select for tumor cells expressing the IL-2tm plasmid or the pCMV2b plasmid. Untransfected control cells were universally killed by this concentration of G418. Transfected cells were allowed to grow for an additional two to three weeks. Total RNA from 106 cultured cells was subsequently isolated using TRI reagent (Molecular Research Center, INC., Cincinnati, Ohio). In order to remove residual plasmid DNA, the isolated RNA was treated with 0.6 µl of DNAs (Life Technologies, Gaithersburg, Md.) followed by phenol/chloroform extraction. Reverse transcription of mRNA was performed under the following conditions: 200 ng total RNA, 1.0 µl M-MLV-reverse transcriptase (200 units/µl), 1 hr incubation at 37° C. PCR was performed on the IL-2tm and pCMV2b cDNA using primers spanning the IL-2 gene and the transmembrane fusion domain as previously described.

Western Blot Analysis of IL-2tm Protein Expression in RD995 Tumor Cells

One million RD995 cells transfected with IL-2tm using (2.0 µg of IL-2tm and 10 µl of Lipofectin) were grown in a six well plate containing 5 ml of RPMI-1640 culture media without G418. Tumor cells were harvested at days 1-5. One million harvested cells were washed twice in PBS and lysed in RIPA buffer containing protease inhibitors (phenylmethyl sulfonyl fluoride, 200 mM; aprotinin, 1 mg/ml; trypsin/chymotrypsin inhibitor, 1 mg/ml; leupeptin, 1 mg/ml; pepstatin A, 1 mg/ml) (Sigma Chemical Company, St. Louis, Mo.). The lysate was sonicated for 10 sec (on ice) and stored at −20° C. until Western blot analysis was performed. Prior to blotting, samples were thawed and 50 µl of lysate was added to 50 µl of 2% SDS and boiled for 5 minutes. Twenty microliters of each sample was then applied to a 12.5% PAGE electrophoresis gel (run for 35 min at 200V) and transferred to Immobilon™-P membrane (Millipore, Bedford, Mass.). The membrane was blocked with 5% nonfat dry milk for 2 h. Subsequently, the membrane was washed with Tris-buffered saline-tween (TTBS) and incubated overnight with 1 µg/ml rabbit anti-IL-2 anti-serum (Santa Cruz Biotechnology, Santa Cruz, Calif.) at 4° C. The membrane was again washed with TTBS and incubated with 0.16 µg/ml peroxidase-conjugated anti-rabbit IgG antibody (Santa Cruz Biotechnology, Santa Cruz, Calif.). Excess peroxidase was removed by washing the membrane with TTBS and with one final wash with TRIS-buffered saline (TBS). Finally, the membrane was soaked in Luminol Reagent (Santa Cruz Biotechnology, Santa Cruz, Calif.) for one minute and exposed to X-ray film.

Immunofluorescent Antibody Staining for Membrane Associated IL-2

One million RD995 cells transfected with IL-2tm were washed twice in PBS and incubated one ice for 30 min with rabbit anti-IL-2 antiserum (10 µg/ml) (Santa Cruz Biotechnology, Santa Cruz, Calif.) or with monoclonal mouse anti-flag antibody (10 µg/ml) (Stratagene, La Jolla, Calif.). Cells were then washed with cold PBS+1% sodium azide and incubated for 30 min with anti-rabbit Alexa 568 (10 µg/ml) (Molecular Probes, Eugene, Oreg.) or with anti-mouse Alexa 488 (10 µg/ml), respectfully. Parental RD995 cells and RD995 transfected with empty vector were similarly stained as negative controls. The cells were permeablized with 0.1% Triton X-100 (Bio-Rad, Richmond, Calif.) and 0.1% sodium citrate buffer incubated on ice for two minutes. After permeablizing the cell membrane, TO-PRO3™ (1 µM) (Molecular Probes, Eugene, Oreg.) was added to stain the nucleus. Cells were then fixed in 1% paraformaldehyde for 30 min at room temperature. An Olympus Fluoview 200 laser scanning confocal microscope was used to visualize the subcellular localization of IL-2 in cells.

Evaluation of Growth of RD995 Cells Transfected with IL-2tm in C3H/HEN Mice

RD995 is a murine spindle cell skin cancer derived from an UV-irradiated C3H/HEN mouse. Groups of ten C3H/HEN mice (Charles River Laboratories, Wilmington, Mass.) were implanted subcutaneously with 106, 5×105 or 105 IL-2tm transfected RD995. Equivalent numbers of pCMV2b transfected tumor cells or parental tumor cells were implanted to serve as a control. The maximum cross sectional dimensions of each tumor were measured every other day with calipers and the area of the tumor was calculated.

PCR Analysis of IL-2tm Gene Expression in Excised RD995 Tumors

On day 40 of tumor growth, mice were sacrificed and tumors excised to evaluate for IL-2tm gene persistence. Total RNA was extracted using TRI reagent and RT-PCR was performed using IL-2tm primers that spanning the fusion gene product as previously described.

Tritiated Thymidine ([3H]-TdR) Uptake by Transfected RD995 Tumors In Vitro

In order to measure whether IL-2tm transfection altered tumor proliferation, 105 RD995 tumor cells (transfected either with IL-2tm, pCMV2b or 105 non-transfected RD995) were placed into each well of a 96-well tissue culture plate (24 replicates). Cells were incubated with 10 µl of [3H]-TdR (50

μCi/ml) per well (NEN™ Life Science Products, Boston, Mass.) at 37° C. for 48 hours. A PHD™ Cell harvester (Cambridge Technology Inc., Cambridge, Mass.) was used to harvest cellular DNA onto glass fiber filters (Gelman Sciences Inc., Ann Arbor, Mich.) and to wash away unincorporated [3H]-TdR. The filter paper was allowed to air dry at room temperature for 4 hrs, placed in 2 ml of scintillation fluid (Perkin Elmer Life Sciences, Boston, Mass.) and counted for one minute/sample on a 2500 TRI-CARB liquid scintillation analyzer (Perkin Elmer Life Sciences, Boston, Mass.).

Evaluation of Biologic Activity of IL-2tm Using the IL-2 Dependent Cell Line CTLL-20

In order to test whether the tumor cell expressed IL-2tm protein was biologically active, IL-2tm transfected tumor cells were lysed and added to the IL-2 dependent T cell line CTLL-20. Lysis of 5×106 RD995 cells transfected with IL-2tm or pCMV2b was accomplished by snap freezing in liquid nitrogen. The membrane portion of the lysate was separated from the cytosol by centrifugation for 15 min at 12,000×g. The cytosol portion was placed into another tube and the membrane portion was reconstituted in an equivalent volume (0.5 ml) of RPMI media. One hundred microliters of membrane lysate or cytosol lysate (serial two-fold dilutions) were placed into a 96 well plate (in triplicate). One hundred thousand CTLL-20 cells were added to each well. CTLL-20 is an IL-2 dependent cell line derived from a C57BL/6 mouse (gift from D. Keith Bishop, University of Michigan Medical School). Prior to starting this experiment, IL-2tm expression in transfected RD995 cells was verified using RT-PCR and primers that span the IL-2 gene and transmembrane domain as previously described. A positive control consisted of serial dilutions of 200 IU recombinant hIL-2 (Chiron, Emeryville, Calif.). The plates were allowed to incubate at 37° C. for 48 hours, and then each well was pulsed with 10 μl of [3H]-TdR (50 μCi/ml) for 24 h. After harvesting, samples were evaluated by scintillation counting.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A nucleic acid molecule encoding a fusion protein comprising;
human interleukin-2 and a transmembrane domain of a protein, wherein the fusion protein enhances the activation of cytotoxic tumor-infiltrating lymphocytes within tumors, and wherein the nucleic acid molecule comprises the nucleotide sequence of SEQ ID NO: 2.

2. An expression vector comprising the nucleotide sequence encoding the fusion protein of claim 1.

3. The expression vector of claim 2, wherein the transmembrane domain of the fusion protein encoded by the expression vector is a subunit of the FC epsilon receptor.

4. The expression vector of claim 3, wherein the transmembrane domain of the fusion gene is a transmembrane domain of FC epsilon-gamma.

5. The expression vector of claim 2, wherein the nucleotide sequence further encodes a tagging protein.

6. The expression vector of claim 5, wherein the tagging protein is FLAG.

7. The expression vector of claim 6, comprising the nucleotide sequence of SEQ ID NO: 13.

8. The expression vector of claim 2, further comprising an enhancer.

9. The expression vector of claim 8, comprising the nucleotide sequence of SEQ ID NO: 15.

10. A method of producing a polypeptide comprising the amino acid sequence of the polypeptide in a cell comprising;
providing an expression vector encoding SEQ ID NO: 11, introducing the expression vector into a cell; maintaining the cell under conditions permitting expression of SEQ ID NO: 11 in the cell, and isolating the polypeptide produced.

11. The method of claim 10, wherein the expression vector comprises the nucleotide sequence of SEQ ID NO: 1.

12. The method of claim 10, wherein a transmembrane domain of SEQ NO: 11 encoded by the expression vector is a subunit of the FC epsilon receptor.

13. The method of claim 12, wherein the transmembrane domain of SEQ ID NO: 11 encoded by the expression vector is a transmembrane domain of FC epsilon-gamma.

14. The method of claim 10, wherein the expression vector comprises the nucleotide sequence of SEQ ID NO: 13.

15. The method of claim 10, wherein the expression vector is a mammalian expression vector.

16. The method of claim 15, wherein the expression vector is pCMV2b.

17. The method of claim 10, wherein the expression vector further encodes a tagging protein.

18. The method of claim 17, wherein the tagging protein is FLAG.

* * * * *